US011091512B2

(12) United States Patent
Saint-Remy

(10) Patent No.: US 11,091,512 B2
(45) Date of Patent: Aug. 17, 2021

(54) MODULATION OF ANTIGEN IMMUNOGENICITY BY DELETING EPITOPES RECOGNIZED BY NKT CELLS

(71) Applicant: Jean-Marie Saint-Remy, Grez-Doiceau (BE)

(72) Inventor: Jean-Marie Saint-Remy, Grez-Doiceau (BE)

(73) Assignee: Imnate Sarl, Strassen (LU)

( * ) Notice: Subject to any disclaimer, the term of this patent is extended or adjusted under 35 U.S.C. 154(b) by 399 days.

(21) Appl. No.: 15/650,784

(22) Filed: Jul. 14, 2017

(65) Prior Publication Data
US 2018/0009843 A1 Jan. 11, 2018

Related U.S. Application Data

(62) Division of application No. 13/989,352, filed as application No. PCT/EP2011/070911 on Nov. 24, 2011, now Pat. No. 9,732,118.

(30) Foreign Application Priority Data

Nov. 25, 2010 (EP) .................................... 10192568

(51) Int. Cl.
| | |
|---|---|
| *C07K 14/755* | (2006.01) |
| *C12N 15/09* | (2006.01) |
| *G01N 33/50* | (2006.01) |
| *C07K 2/00* | (2006.01) |
| *C07K 14/415* | (2006.01) |
| *C12N 9/64* | (2006.01) |
| *A61K 39/00* | (2006.01) |
| *C07K 16/00* | (2006.01) |
| *C07K 14/435* | (2006.01) |
| *C12N 5/0783* | (2010.01) |

(52) U.S. Cl.
CPC .............. *C07K 2/00* (2013.01); *A61K 39/001* (2013.01); *C07K 14/415* (2013.01); *C07K 14/43531* (2013.01); *C07K 14/755* (2013.01); *C07K 16/00* (2013.01); *C12N 9/641* (2013.01); *A01K 2207/12* (2013.01); *A61K 2039/577* (2013.01); *C07K 2317/524* (2013.01); *C07K 2317/526* (2013.01); *C12N 2710/10322* (2013.01); *C12N 2710/10343* (2013.01)

(58) Field of Classification Search
None
See application file for complete search history.

(56) References Cited

U.S. PATENT DOCUMENTS

| | | | |
|---|---|---|---|
| 2003/0099647 A1 | 5/2003 | Deshpande et al. | |
| 2010/0233119 A1 | 9/2010 | Josephson | |

FOREIGN PATENT DOCUMENTS

| | | |
|---|---|---|
| RU | 2008 140 732 A | 4/2010 |
| WO | WO 02/19968 A2 | 3/2002 |
| WO | WO 2010/037395 A2 | 4/2010 |
| WO | WO 2010/037402 A1 | 4/2010 |
| WO | WO 2010/065544 A2 | 6/2010 |

OTHER PUBLICATIONS

Girardi et al(JBC, 2016, 291(20): 10677-10683) (Year: 2016).*
Bagoly et al (Front. Neurol. 2019, pp. 1-24) (Year: 2019).*
Chapin and Hajjar (Blood Rev. 2015, 2991: 17-24) (Year: 2015).*
Mazurkiewicz-Pisarek et al (Acta, Biochimica Polonica, 2016, 63(1): 11-16) (Year: 2016).*
UniprotKB-P00451, Dec. 2020 (Year: 2020).*
Arrenberg et al., "Oligoclonality and innate-like features in the TCR repertoire of type II NKT cells reactive to a beta-linked self-glycolipid," *Proceedings of the National Academy of Sciences USA*, vol. 107, No. 24, pp. 10984-10989 (2010).
Brutkiewicz, *Journal of Immunology*, vol. 177, pp. 769-775 (2006).
Burrows et al., *Nature Immunology*, vol. 10, No. 7, pp. 669-671 (2009).
Castano et al., "Peptide Binding and Presentation by Mouse CD1," *Science*, vol. 269, No. 5221, pp. 223-226 (1995).
Godfrey et al., "Raising the NKT cell family," *Nature Immunology*, vol. 11, No. 3, pp. 197-206 (2010).
Lee et al., "Induction of an Antigen-specific, CD1-restricted Cytotoxic T Lymphocyte Response In vivo," *Journal of Experimental Medicine*, vol. 187, No. 3, pp. 433-438 (1998).
Matsuda et al., "CD1d-restricted iNKT cells, the 'Swiss-Army knife' of the immune system," *Current Opinion in Immunology*, vol. 20, No. 3, pp. 358-368 (2008).
Schnolzer et al., "In situ neutralization in Boc-chemistry solid phase peptide synthesis. Rapid, high yield assembly of difficult sequences.," *Int. J Pept. Protein Res.*, vol. 40, pp. 180-193 (1992)—Abstract.

(Continued)

*Primary Examiner* — G. R. Ewoldt
*Assistant Examiner* — Marianne DiBrino
(74) *Attorney, Agent, or Firm* — Leydig, Voit & Mayer, Ltd.

(57) ABSTRACT

The invention describes a method and compounds for the prevention of immune responses towards allofactors, towards viral vectors used for gene therapy and gene vaccination, towards proteins to which subjects are naturally exposed, towards genetically-modified organisms and towards undesirable effects related to vaccine administration for allergic or infectious diseases.

4 Claims, 3 Drawing Sheets

Specification includes a Sequence Listing.

(56) References Cited

OTHER PUBLICATIONS

Scott et al., "Dendritic Cells Permit Identification of Genes Encoding MHC Class II-Restricted Epitopes of Transplantation Antigens," *Immunity*, vol. 12, pp. 711-720, (2000).
Tam et al., "Methods and Strategies of Peptide Ligation," *Biopolymers*, vol. 60, pp. 194-205 (2001).
Tangri et al., "Presentation of Peptide Antigens by Mouse CD1 Requires Endosomal Localization and Protein Antigen Processing," *Proceedings of the National Academy of Sciences USA*, vol. 95, No. 24, pp. 14314-14319 (1998).
Texier et al., "HLA-DR Restricted Peptide Candidates for Bee Venom Immunotherapy," *The Journal of Immunology*, vol. 164, No. 6, pp. 3177-3184 (2000).
European Patent Office, International Search Report in International Application No. PCT/EP2011/070911 dated Mar. 8, 2012.
Girardi et al. *Journal of Biological Chemistry*, 291(20): 10677-10683 (2016).
Swaroop et al. "Mutagenesis of a Potential Immunoglobulin-binding Protein-binding Site Enhances Secretion of Coagulation Factor VIII," *Journal of Biological Chemistry*, vol. 272, No. 39, pp. 24121-24124 (1997).
FDA Approval Letter for Myozyme™ (acid a-1,4 glucosidase) FDA Application No. 125141/0 dated 2006.
Schoser et al., "Therapeutic Approaches in Glycogen Storage Disease Type II/Pompe Disease," *Neurotherapeutics:*, 5(4), pp. 569-578 (2008).
Kohler et al., "Pompe Disease: From Basic Science to Therapy," *Neurotherapeutics*, vol. 15, pp. 928-942 (2018).

\* cited by examiner mannoside and alpha-glucuronosylceramide. The present consensus (see reviews, such as Matsuda et al, Current Opinion in Immunology 2008, 20:358-368 and Godfrey et al, Nature reviews Immunology 2010, 11: 197-206) is that CD1d binds only ligands containing lipid chains, or in general a common structure made of a lipid tail which is buried into CD1d and a sugar residue head group that protrudes out of CD1d.

Peptides are not deemed to be able to activate NKT cells through presentation by CD1d. It was, however, suggested that long hydrophobic peptides containing bulky aminoacid residues could bind to CD1d (Castano et al, Science 1995, 269: 223-226). Observations carried out using phage display libraries expressing random sequence peptides with no defined physiological relevance, allowed establishing a theoretical consensus motif (Castano et al, Science 1995, 269: 223-226 and see below).

In fact, Castano et al show that the cells which are activated are CD8+ T cells, namely MHC class I restricted cells, and not NKT cells. These findings teach the one skilled in the art that there is no evidence that hydrophobic peptides are presented by CD1d molecules. The physiological relevance of the claims made by Castano et al was further questioned due to the inability to elicit NKT cells under conventional immunization protocols (Matsuda et al, Current Opinion in Immunology 2008, 20:358-368 and Brutkiewicz Journal of Immunology 2006, 177: 769-775). Artificial systems such as immunization with cells transfected to overexpress CD1d and loaded in vitro with an ovalbumin-derived peptide were able to elicit NKT cells. Likewise, intradermal immunization with plasmid DNA together with murine CD1d and costimulatory molecules induce cytolytic CD1d-restricted T cells (Lee et al, Journal of Experimental Medicine 1998, 187: 433-438). Hydrophobic peptides containing a structural motif made of an aromatic residue in position P1 and P7, and an aliphatic chain in position P4 were claimed by Castano et al (Science 269: 223, 1995) to contain a core motif for CD1d binding epitopes. As described above, the conclusions reached by Castano et al are not supported by data.

We made the unexpected finding that peptides encompassing a hydrophobic aminoacid sequence are in fact capable of eliciting activation of NKT cells.

If epitopes from proteins administrated for therapeutic purposes, or to which subjects are normally exposed, or when gene therapy or gene vaccination is carried out, or administered in the context of vaccination for allergic or infectious diseases bind to CD1d and thereby activate NKT cells, then alteration of said proteins by mutations and/or deletions to eliminate said epitopes would be highly desirable to prevent immunogenicity.

Identification of such epitopes followed by mutation, addition or deletion of aminoacids to prevent activation of NKT cells forms the basis of the present invention.

SUMMARY OF THE INVENTION

The present invention relates to the use of peptides or polypeptides for the treatment of immune responses elicited towards allofactors in a subject by preventing such immune response towards said allofactors.

The present invention also relates to the use of peptides or polypeptides for the treatment of immune responses elicited towards viral vectors used for gene therapy or gene vaccination in a subject by preventing such immune response towards said viral vectors.

The present invention also relates to the use of peptides or polypeptides made by genetically-modified organisms for the prevention in a subject of immune responses elicited by exposure to natural proteins.

The present invention further relates to the use of peptides or polypeptides for vaccination purposes when activation of innate immunity is detrimental.

The present invention also relates to methods to identify proteins which carry CD1d binding epitopes and to eliminate such epitopes by aminoacid substitution or deletion.

We made the unexpected finding that a significant proportion of peptides or polypeptides carried aminoacid sequences which allow them to bind and to be presented by CD1d determinants for activation of natural killer T (NKT) cells. Activation of such cells results in release of cytokines and, in some cases, in acquisition or increase of cytolytic properties.

The present invention relates in one aspect to the use of at least one isolated peptide or polypeptide used as an allofactor, which has been modified to eliminate at least one hydrophobic amino acid residue involved in the formation of an epitope recognized by NKT cells, as a medicament for preventing in a subject immune responses to said allofactor.

The present invention also relates in one aspect to the use of at least one isolated peptide or polypeptide used as a viral vector for gene therapy or gene vaccination, which has been modified to eliminate at least one hydrophobic amino acid residue involved in the formation of an epitope recognized by NKT cells, as a medicament for preventing in a subject immune responses to said viral vectors.

The present invention also relates in one aspect to the use of at least one isolated peptide or polypeptide produced by a genetically-modified organism, said peptide or polypeptide being modified to eliminate at least one hydrophobic amino acid residue involved in the formation of an epitope recognized by NKT cells, as a medicament for preventing in a subject immune responses to natural exposure to said peptides or polypeptides.

The present invention further relates in one aspect to the use of at least one isolated peptide or polypeptide used as a vaccine, which has been modified to eliminate at least one hydrophobic amino acid residue involved in the formation of an epitope recognized by NKT cells, as a medicament for preventing in a subject an unwanted or inappropriate immune response to said vaccine.

In a further aspect, the invention also covers the use of at least one isolated peptide or polypeptide used as an allofactor, a viral vector, a genetically-modified organism or a vaccine, which has been modified to eliminate at least one hydrophobic amino acid residue involved in the formation of an epitope recognized by NKT cells, as a medicament for preventing in a subject activation, cytokine production, cytolytic activity and suppressive activity on adaptive immune responses carried by CD4+ NKT cells in said subject.

The present invention relates to hydrophobic peptides or polypeptides encompassing at least one CD1d-restricted T cell epitope, in which aminoacids positioned as anchoring residues to CD1d are replaced by alternative aminoacids, or deleted, which results in a loss or significant reduction of binding to CD and thereby of NKT cell activation.

The structure of the CD1d molecule indicates that hydrophobic aminoacid residues are required to occupy the two hydrophobic pockets located at the extremities of the CD1d cleft and that an aliphatic residue should occupy the position in the middle of the cleft. Therefore, as a general example of CD1d binding sequence, the motif [FW]-xx-[ILM]-xx-

[FWTH] can be used in which [FW] indicates that either F or W can occupy the first anchoring residue (P1), that the P4 position can be occupied by either I, L or M and that P7 can be occupied by F, W, T or H. x in this general model motif stands for any aminoacid. It should be clear for the one skilled in the art that various combinations of these aminoacid residues are possible. In a particular embodiment the general model motif can be presented as a reverted sequence such as [FWTH]-xx-[ILM]-xx-[FW]. In yet another particular embodiment at least one aminoacid is added within the CD1d binding motif, which disrupts the motif, prevents its capacity to bind to CD1d and thereby its capacity to activate NKT cells.

The present invention further relates more particularly to peptides or polypeptides wherein F, W, T, H or Y in positions P1 and P7 are replaced by a non-natural amino acid (for example a D-aminoacid) or by an organic compound.

In any of the above uses said allofactor may be any peptide or polypeptide used: (1) for replacement therapy for coagulation defects or fibrinolytic defects, including factor VIII, factor IX and staphylokinase; (2) hormones such as growth hormone or insulin; (3) cytokines and growth factors, such as interferon-alpha, interferon-gamma, GM-CSF and G-CSF; (4) antibodies for the modulation of immune responses, including anti-IgE antibodies in allergic diseases, anti-CD3 and anti-CD4 antibodies in graft rejection and a variety of autoimmune diseases, anti-CD20 antibodies in non-Hodgkin lymphomas; (5) erythropoietin in renal insufficiency and; (6) genetically modified antigens.

In any of the above uses said viral vector may be any peptide or polypeptide of RNA viruses (gamma-retroviruses and lentiviruses) or DNA viruses (adenoviruses, adeno-associated viruses, herpes viruses and poxviruses).

In any of the above uses said genetically-modified organism may be any organism of plant or animal origin, which is used as food or feed, for producing crops or manufacture material, or for producing transgenic animals for food or feed, or stock breeding.

In any of the above, said peptide or polypeptide used for vaccination may be from allergens or from infectious agents, including viruses, bacteria and parasites. Allergens may be airborne allergens such as those derived from house dust mite, from pollens or from domestic animals, food allergens such as peanut, ovalbumin, cereals, fruits and legumes, and contact antigens such as latex. Diseases characterizing allergen sensitization include allergic asthma, allergic rhinosinusitis, anaphylactic shock, urticaria, atopic dermatitis and contact dermatitis.

The present invention also relates to methods for identifying peptides or polypeptides activating NKT cells and eliminates such activation by altering CD1d binding epitopes by substitution, addition or deletion of aminoacids. Said methods comprise the steps of incubating said peptide or polypeptide with cells carrying CD1d, followed by addition of a population of polyclonal NKT cells and determination of activation of said NKT cells.

The invention further encompasses isolated viral vectors characterized in that they comprise at least one peptide or polypeptide of an allofactor modified by substitution or deletion of at least one hydrophobic aminoacid, or at least one peptide or polypeptide from an allergen or from a infectious agent modified by substitution or deletion of at least one hydrophobic aminoacid residue. It should be understood that the viral vector itself may also be modified by substitution or deletion of hydrophobic aminoacid residues.

Definitions

The term “peptide” when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification. The term “polypeptide” when used herein refers to generally longer peptides or proteins.

The term “epitope” when used herein refers to one or several portions (which may define a conformational epitope) of a protein which is/are specifically recognized and bound by an antibody or a portion thereof (Fab', Fab2', etc.) or a receptor presented at the cell surface of a B or T cell lymphocyte, and which is able, by said binding, to induce an immune response.

The term “antigen” when used herein refers to a structure of a macromolecule comprising one or more hapten(s) and/or comprising one or more T cell epitopes. Typically, said macromolecule is a protein or peptide (with or without polysaccharides) or made of proteic composition and comprises one or more epitopes; said macromolecule can herein alternatively be referred to as “antigenic protein” or “antigenic peptide”.

The term “allergen” refers to a specific subset of antigen characterized by its capacity to elicit antibodies of the IgE isotype in predisposed individuals.

The term “T cell epitope” or “T-cell epitope” in the context of the present invention refers to a dominant, sub-dominant or minor T cell epitope, i.e., a part of an antigenic protein that is specifically recognized and bound by a receptor at the cell surface of a T lymphocyte. Whether an epitope is dominant, sub-dominant or minor depends on the immune reaction elicited against the epitope. Dominance depends on the frequency at which such epitopes are recognized by T cells and able to activate them, among all the possible T cell epitopes of a protein. In particular, a T cell epitope is an epitope bound by MHC class I or MHC class II molecules.

The term “NKT cell epitope” refers to a part of an antigenic protein that is specifically recognized and bound by a receptor at the cell surface of a T lymphocyte. In particular, a NKT cell epitope is an epitope bound by CD1d molecules.

The term “CD4+ effector cells” refers to cells belonging to the CD4-positive subset of T-cells whose function is to provide help to other cells, such as, for example B-cells. These effector cells are conventionally reported as Th cells (for T helper cells), with different subsets such as Th0, Th1, Th2, and Th17 cells.

The term “NKT cells” refers to cells of the innate immune system characterized by the fact that they carry receptors such as NK1.1 and NKG2D, and recognize epitopes presented by the CD1d molecule. In the context of the present invention, NKT cells can belong to either the type 1 (invariant) or the type 2 subset.

The “CD1d molecule” refers to a non-MHC derived molecule made of 3 alpha chains and an anti-parallel set of beta chains arranged into a deep hydrophobic groove opened on both sides and capable of presenting lipids, glycolipids or hydrophobic peptides to NKT cells.

The term “immune disorders” or “immune diseases” refers to diseases wherein a reaction of the immune system is responsible for or sustains a malfunction or non-physiological situation in an organism. Immune disorders in the context of the present invention refer to pathology induced by infectious agents and tumor surveillance.

The term "allofactor" refers to a protein, peptide or factor (i.e. any molecule) displaying polymorphism when compared between two individuals of the same species, and, more in general, any protein, peptide or factor that induces an (alloreactive) immune response in the subject receiving the allofactor. By extension, allofactors also include genetically-modified proteins used for feeding.

The term "alloantigen" or "allograft antigen" when used herein refer to an antigen derived from (shed from and/or present in) a cell or tissue which, when transferred from a donor to a recipient, can be recognized and bound by an antibody of B or T-cell receptor of the recipient. Alloantigens are typically products of polymorphic genes. An alloantigen is a protein or peptide which, when compared between donor and recipient (belonging to the same species), displays slight structural differences. The presence of such a donor antigen in the body of a recipient can elicit an immune response in the recipient. Such alloreactive immune response is specific for the alloantigen.

DETAILED DESCRIPTION OF THE INVENTION

Figure 1:
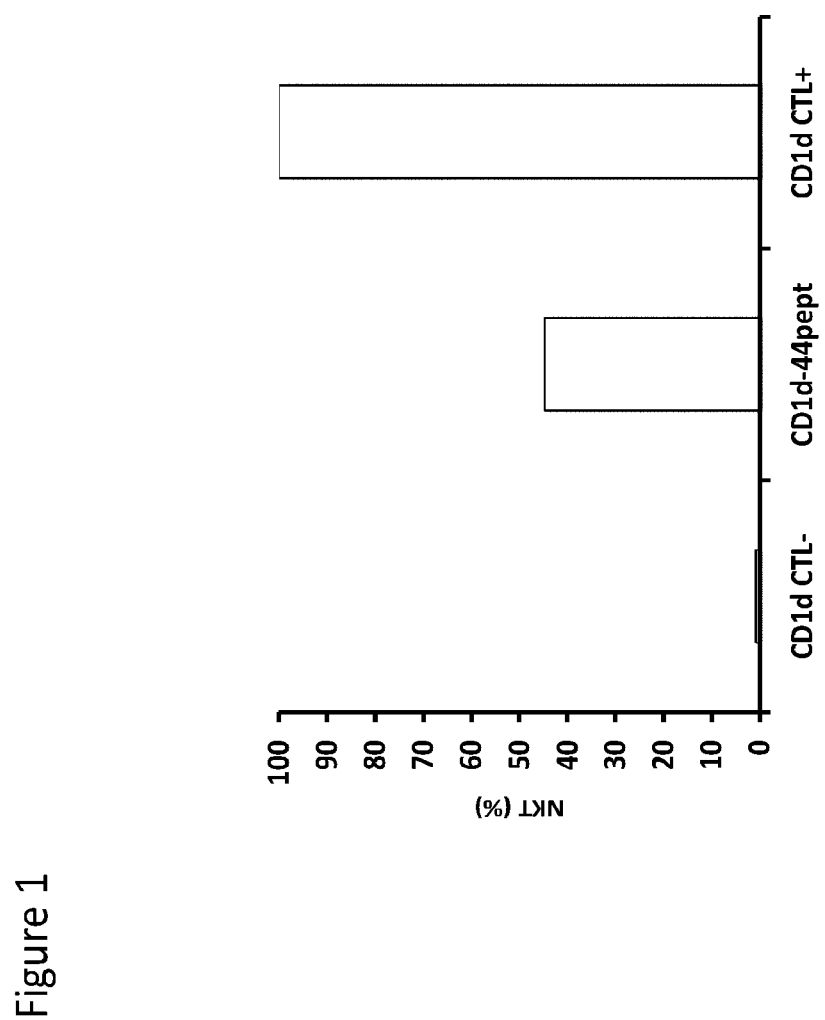
Figure 2:
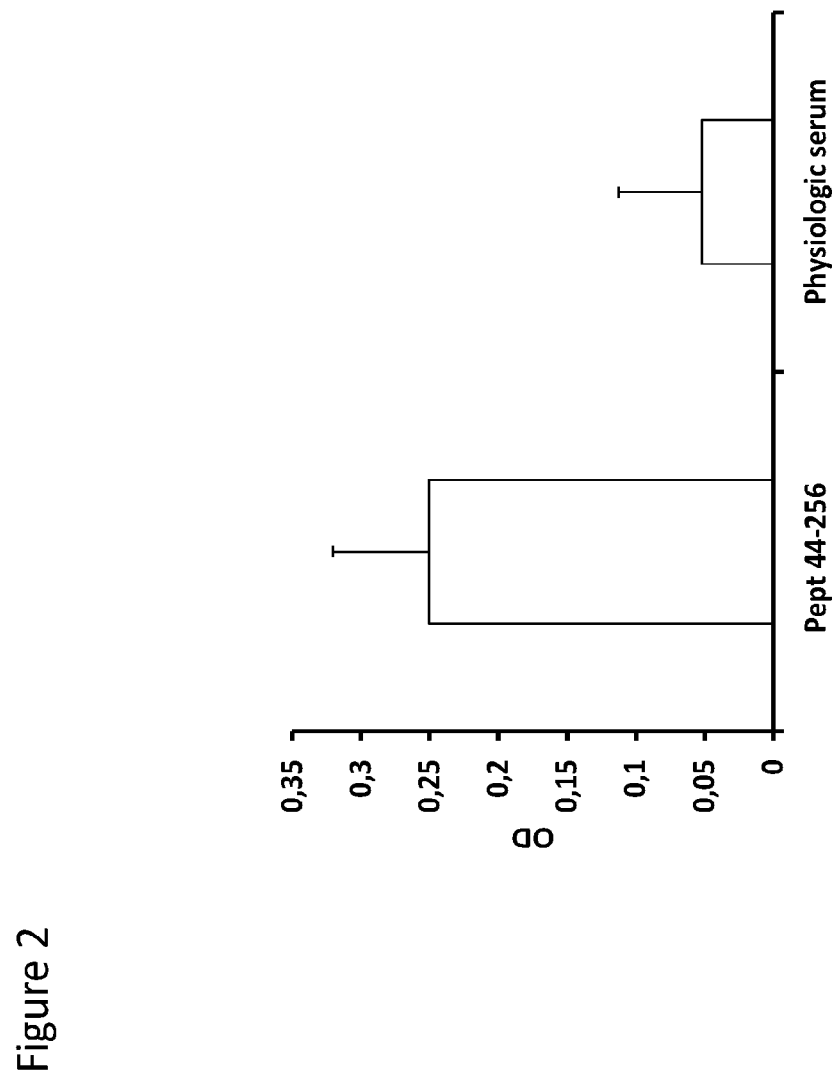
Figure 3:
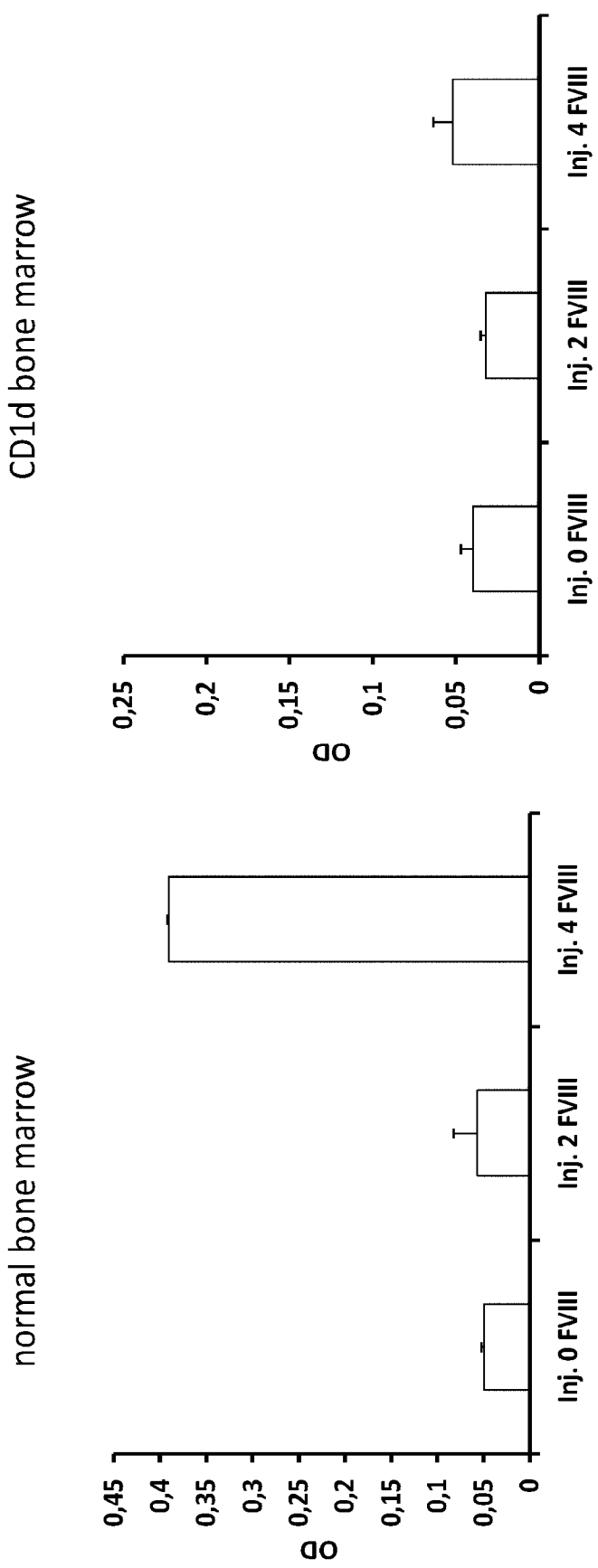

The present invention provides ways to prevent, in a subject, an immune response towards allofactors, towards viral vectors used for gene therapy or gene vaccination, towards proteins used for food or feed, towards proteins to which said subject is exposed by inhalation or by stings, or to prevent, in a subject, an undesirable activation of innate immunity in the use of vaccines towards allergens or infectious agents.

In particular, the invention provides ways to prevent the expansion and functional activity of CD4+ NKT cells. Such cells are usually classified into two distinct subsets, namely type 1 for NKT cells carrying an invariant TCR alpha chain (Valpha14 in the mouse, Valpha24 in humans), or type 2 NKT cells which present with a diverse alpha chain repertoire. However, recent evidence has suggested that alternative subsets of NKT cells which do not fit in the type 1 or type 2 category. It is the purpose of the present invention to include these non conventional NKT cells, provided they carry the CD4 co-receptor. Upon presentation of an antigen bound to CD1d, NKT cells are rapidly activated and secrete a number of cytokines thought to be determinant to influence other cells from both the innate and adaptive immune systems. In some circumstances, said activated NKT cells acquire or increase cytotoxic properties. In yet additional circumstances, said activated NKT cells suppress or reduce the elicitation of an adaptive immune response by interaction with class II-restricted CD4+ T cells.

In the context of the present invention, we made the unexpected observation that peptides can be presented by the CD1d molecule. A characteristic of the CD1d molecule is that it is made of two anti-parallel alpha chains forming a cleft sitting atop of a platform made of two anti-parallel beta chains. The cleft is narrow and deep and accept only hydrophobic residues, classically deemed to be only lipids. The cleft can accommodate a sequence of 7 aminoacids characterized as a hydrophobic residue in position (P)1 and 7, and an aliphatic residue in P4. P1 is an obligate hydrophobic residue, such as F, W, H or Y. However, P7 is permissive and can contain alternative residues provided they are not polar. Residues in P4 are preferably aliphatic but are optional. A general sequence for a CD1d binding motif is therefore [FWTHY]-$X_2X_3$-[ILMV]-$X_5X_6$-[FWTHY]. It should however be clear for those skilled in the art that the motif is symetrical and that P7 can be considered as P1, and P1 can be considered as P7. The general sequence of a CD1d binding motif is provided here as a general indication without any limiting intention. Peptides and polypeptides considered for application of the present invention are defined according to their capacity to activate NKT cells by presentation into CD1d molecule.

Hydrophobic peptides or polypeptides capable of activating NKT cells and, consequently, carrying a CD1d-binding motif are found in allofactors, viral vectors, proteins used for food or feed, proteins to which said subject is exposed by inhalation or by stings, genetically-modified proteins and allergens, thereby endowing said allofactor, viral vector, genetically-modified protein or allergen with the capacity to activate CD4+ NKT cells.

The present invention relates to the production of peptides or polypeptides containing CD1d binding motif(s), which confer them with the capacity to activate NKT cells and which are modified by substitution of hydrophobic residues in P1 and/or P7, with, optionally, substitution or deletion of aliphatic residues in P4, or any combination of these, which results in a loss or significant reduction of the capacity of peptides or polypeptides to bind to CD1d and thereby results in a loss or significant reduction of said peptides or polypeptides to activate NKT cells.

In a more particular embodiment, F, W, T, H or Y in positions P1 and/or P7 are replaced by a non-hydrophobic aminoacid residue, or, optionally, I, L, M or V in position P4 is replaced by a non-aliphatic residue, or any combination of these.

In yet another particular embodiment, hydrophobic residues located in position P1 and/or P7, or, optionally, aliphatic residues located in P4, or any combination of these, are replaced by at least one non-natural aminoacid different from non-natural F, W, T, H, Y, or by a non-aromatic organic compound.

In yet another particular embodiment at least one aminoacid is added within the CD1d binding motif, in any location within the P1 to P7 sequence, which disrupts the motif, prevents its capacity to bind to CD1d and thereby its capacity to activate NKT cells.

In a preferred embodiment, non-natural aminoacids are D-aminoacids.

The present invention also relates to the production of peptides or polypeptides containing CD1d binding motif(s), which confer them with the capacity of activate NKT cells, and which are modified by deletion of hydrophobic residues in P1 and/or P7, or, optionally, by deletion of aliphatic residues in P4, or any combination of these, which results in a loss or significant reduction of the capacity of peptides or polypeptides to bind to CD1d and thereby results in a loss or significant reduction of said peptides or poylpeptides to activate NKT cells.

Upon administration to a subject, such peptides or polypeptides are not loaded on CD1d and thereby are prevented from activating NKT cells.

In a further aspect, the invention also covers the use of at least one isolated peptide or polypeptide comprising at least one substitution or deletion of F, W, T, H or Y in positions P1 or P7 for preventing in a subject an immune response towards allofactor administration, viral vector administration, proteins to which said subject is exposed by food, feed, systemic or inhalation route, or allergens or infectious agents used for vaccination purposes.

In yet a further aspect, the invention covers the use of at least one isolated peptide or polypeptide comprising at least one substitution or deletion of F, W, T, H or Y in positions P1 or P7 for preventing in a subject the activation of NKT cells towards allofactor administration, viral vector administration, proteins to which said subject is exposed by food, feed, systemic or inhalation route, or some allergens or infectious agents used for vaccination purposes.

In yet a further aspect, the invention also covers the use of at least one isolated peptide or polypeptide comprising at least one substitution or deletion of F, W, T, H or Y in positions P1 or P7 as a medicament for preventing in a subject an immune response towards allofactor administration, viral vector administration, proteins to which said subject is exposed by food, feed, systemic or inhalation route, genetically modified peptides or polypeptides or some allergens or infectious agents used for vaccination purposes.

The number of CD1 d binding motifs when present in a peptide or polypeptide, is very limited. Examples of such peptides or polypeptides are provided below. Typically a polypeptide presents one to five of these motifs.

An additional advantage of the present invention is that the CD1d molecule presents a very limited degree of polymorphism. It is therefore obvious for the one skilled in the art that the same aminoacid substitutions, addition or deletions according to the present invention provide peptides or polypeptides useful for all or a large majority of subjects. This is in sharp contrast with peptide or polypeptide motifs binding to MHC class II molecules, wherein a large number of peptides can be delineated which contain the appropriate sequence. This is due to the minimum constraints imposed to MHC class II binding peptides and to the large polymorphism of class II molecules.

Peptides and polypeptides which are the object of the present invention are identified as follows:

(1) a peptide or polypeptide aminoacid sequence is, optionally, evaluated for the presence of at least one CD1d motif containing an hydrophobic residue in P1 and P7, and an aliphatic residue in P4. A general sequence such as [FWTHY]-$X_2X_3$-[ILMV]-$X_5X_6$-[FWTHY] can be used for using algorithms well known in the art such as expasy.org/tools/scanprosite/

This general sequence should be considered as a tool to help identifying which sequence(s) in said peptide or polypeptide contain a motif which could enable said peptide or polypeptide to activate NKT cells.

(2) the capacity of the peptide or polypeptide to bind to CD1d and to activate NKT cells is tested in vitro using a cell line expressing the CD1d molecule. Examples of such cell lines are known in the art (for instance JAW S2 cells). In a preferred embodiment, the cell line is not presenting MHC class II molecules and is transduced for hyperexpression of CD1d using a viral vector containing the DNA sequence of CD or any other means known in the art to introduce a gene in a cell. Methods for cell transduction are known in the art. The cell line is loaded in culture with the peptide or polypeptide, or with a synthetic peptide encompassing the corresponding sequence. Such synthetic peptides are easily produced by synthesis, using for instance the fmoc solid phase synthesis well known in the art. Efficient presentation of the peptide, polypeptide or corresponding synthetic peptide by the CD1d molecule is then evaluated by measuring the activation of NKT cells. Such cells can be obtained from peripheral blood by, for instance, magnetic sorting and maintained in culture with stimulants such as alpha-galceramide, in the presence of cytokines such as IL-2, IL-15 or IL-7. These methods are described in the art (see for instance Godfrey et al, Nature Reviews. Immunology 2010, 11: 197-206). Activation of NKT cells is assessed using methods such as evaluation of cytokine production.

Alternatively, peptides actually presented by APC in CD1d molecules can be eluted and separated by various chromatography methods. Full description of such methodology will be found in Scott et al, Immunity, 12: 711-720, 2000. Said peptides are then sequenced to identify which aminoacid residues are located in P1 and P7.

Alternatively, said synthetic peptides can be loaded on tetramers of the CD1d molecule to detect NKT cells specific for such peptide. One possibility is to use fluorescence-labeled tetramers and detection using a fluorescence-activated cell sorting system (facs).

(3) the aminoacid sequences identified as being able to activate NKT cells and, optionally, identified by algorithms, are then modified by either substitution or deletion. In a preferred embodiment, F, W, T, H or Y in positions P1 and/or P7 are replaced by at least one aminoacid different from F, W, T, H, Y. Natural aminoacids can be modified by post-transcriptional modifications or substituted with chemical groups such as methyl groups. In another preferred embodiment, F, W, T, H or Y in positions P1 and/or P7 are replaced by any suitable alternative non-natural aminoacid. Examples of non-natural aminoacid residues are D-aminoacids. In yet another embodiment, F, W, T, H or Y in positions P1 and/or P7 are replaced by at least one aminoacid different from F, W, T, H, Y. In another preferred embodiment, F, W, T, H or Y in position P1 is replaced by at least one aminoacid different from F, W, T, H, Y, by any suitable alternative non-natural aminoacid or by a non-aromatic organic compound. Such aminoacid substitution is obtained using methods well known in the art. In yet a further preferred embodiment, F, W, T, H or Y in position P1 is deleted. In yet another embodiment, F, W, T, H or Y in positions P1 and P7 are deleted. Methods to carry out said deletions are well known in the art. In yet another particular embodiment at least one aminoacid is added within the CD1d binding motif, in any location within the P1 to P7 sequence.

According to the present invention medicaments are envisaged for the treatment of diseases wherein administration of allofactors are required, such as in:

(1) congenital or acquired deficiency in factors associated with coagulation (such as factor VIII, factor IX or factor X) or fibrinolysis, with defect in enzymes associated with the metabolism of polysaccharides or glycogen (such as in Pompe disease), or with defect in hormone production (such as insulin in diabetes or growth hormone in nanism)

(2) acute or chronic situations wherein it is advantageous to administer a curative agent, such as thrombolytic agents including staphylokinase and microplasmin, (3) disorders of the immune system in which it is required to administer cytokines (or their receptor) or growth factors (such as interferon-alpha, interferon-beta, interferon-gamma, G-CSF, GM-GSF, KGF or erythropoietin)

(4) diseases characterized by chronic inflammation or inappropriate immune responses, wherein therapeutic antibodies should be administered, including anti-tumor necrosing factor, anti-CD3 or anti-CD4 antibodies in autoimmune diseases and graft rejection, antibodies to lymphocyte surface markers (such as anti-CD20 antibodies in non-Hodgkin lymphomas), or antibodies to factor VIII in the prevention of thrombosis. The list of therapeutic antibodies is growing fast and the present invention intends to cover the use of any antibodies used for therapeutic purposes in general.

According to the present invention medicaments are also envisaged for use in gene therapy and gene vaccination, wherein viral vectors are utilized and wherein the immune response against said vectors precludes transgene expression.

According to the present invention medicaments are also envisaged for diseases elicited by exposure to environmental proteins, such as:

(1) proteins to which said subject is exposed by food or feed. Examples of these are cereals such as wheat, maize, rice, soybean and colza, vegetables such as potato and beetroot, fruits such as rosacea, nuts, and avocado, enzymes, anti-viral or anti-bacterial drugs.

(2) proteins towards which the subject is exposed by inhalation, systemic route or by stinging. Examples of these are allergic reactions to pollens, contact reaction to latex or hymenoptera stings.

According to the present invention medicaments are also envisaged for immunization (vaccination) such as:

(1) vaccination against allergens (2) vaccination against infectious agents, including viruses, bacteria and parasites In both these circumstances it may be advantageous to prevent an activation of the innate immune system so as to prevent excess of inflammation and its detrimental consequences on the result of said vaccination. Another advantage in the setting of vaccination to allergens or infectious agents is that the elimination of NKT cell activation prevents the suppressive effect of activated NKT cells on the developemnt of an adaptive response against said allergens or said infectious agents.

It should be recognized that the above list is not exhaustive and that the invention intends to cover newly-introduced products such as antibodies, cytokines, growth factors or peptides and polypeptides used for replacement in congenital or acquired deficiencies, and genetically-modified proteins.

It should be understood that any of the peptides or polypeptides listed above may be administered in the form of gene for transgenesis, which may be carried out using viral vectors or other means known by those skilled in the art. In such a case, the viral vector itself may be modified according to the present invention by eliminating CD1d binding motifs.

The medicament of the invention is usually, though not necessarily, a (pharmaceutical) formulation comprising as active ingredient at least one of the peptides or polypeptides of the invention or a gene therapeutic vector capable of expressing said peptides or polypeptides. Apart from the active ingredient(s), such formulation will comprise at least one of a (pharmaceutically acceptable) diluent.

A notable exception to this rule is the use of proteins from genetically-modified organisms for food or feed, exposure by inhalation or by the systemic route.

In general, administration of peptides or polypeptides of the invention prevents activation of the innate immune system, more particularly activation of NKT cells, more particularly the production of cytokines associated with NKT cell activation.

The route of administration for peptides or polypeptides of the present invention may vary according to the indication and/or the nature of the peptides or polypeptides. Examples are intravenous injection of coagulation factors, subcutaneous injection of insulin and oral administration of genetically-modified proteins. The present invention intends to cover all other possible routes of administration such as intranasal, sublingual, percutaneous, intramuscular, intrarectal or intravaginal.

As explained in detail further on, the peptides or polypeptides of the present invention can be made by chemical synthesis, which further allows the incorporation of non-natural amino acids. The peptides or polypeptides of the present invention can also be produced using methods know in the art for the production of recombinant proteins using expression systems such as bacterial cells, yeast cells, insect cells, plant cells or mammalian cells.

Another aspect of the present invention relates to methods for generating peptides and polypeptides of the present invention described herein. Such methods include the identification of NKT-cell epitopes from allofactors, viral vectors, proteins to which said subject is exposed by food, feed, systemic or inhalation route, allergens or specific infectious agents. Ways for in vitro and in silico identification NKT-cell epitopes are amply known in the art and some aspects are elaborated upon hereafter.

The identification of a NKT-cell epitope in the context of the present invention is known to a person skilled in the art. For instance, peptide sequences isolated from allofactors, viral vectors, proteins to which said subject is exposed by food, feed, systemic or inhalation route, genetically-modified proteins, allergens or specific infectious agents are tested by, for example, NKT cell biology techniques, to determine whether the peptide sequences elicit a NKT cell response. Those peptide sequences found to elicit a NKT cell response are defined as having NKT cell stimulating activity. Mammal NKT cell stimulating activity can further be tested by culturing NKT cells obtained from an individual sensitized to an allofactor, viral vector, proteins to which said subject is exposed by food, feed, systemic or inhalation route, genetically-modified protein, allergen or specific infectious agent, and determining whether proliferation of NKT cells occurs in response to the peptide/epitope as measured, e.g., by cellular uptake of tritiated thymidine. Stimulation indices for responses by NKT cells to peptides/epitopes can be calculated as the maximum CPM in response to a peptide/epitope divided by the control CPM. A NKT cell stimulation index (S.I.) equal to or greater than two times the background level is considered "positive." Positive results are used to calculate the mean stimulation index for each peptide/epitope for the group of peptides/epitopes tested. Non-natural NKT-cell epitopes can further optionally be tested for their binding affinity to CD1d molecules. The binding of non-natural NKT-cell epitopes to CD1d molecules can be performed in different ways. For instance, soluble CD1d molecules are obtained and made tetrameric by synthesis and/or chemical coupling. The CD1d molecule is purified by affinity chromatography. Soluble CD1d molecules are incubated with a biotin-labeled reference peptide produced according to its strong binding affinity for said CD1d molecule. Peptides to be assessed for CD1d binding are then incubated at different concentrations and their capacity to displace the reference peptide from its CD1d binding site is calculated by addition of neutravidin. Methods can be found in for instance in Texier et al., (2000) J. Immunology 164, 3177-3184) for peptides presented by the MHC class II determinants, but the method can easily be applied to CD1d-restricted NKT cell epitopes. The immunogenic peptides or polypeptides of the invention have a mean NKT cell stimulation index of greater than or equal to 2. An immunogenic peptide having a NKT cell stimulation index of greater than or equal to 2 is considered useful as a candidate to carry out the substitution or deletion of hydrophobic aminoacid residues, or addition of aminoacids within the sequence of the CD1d binding motif, as described in the present invention.

If two or more aminoacid sequences which share an area of overlap in the native peptide or polypeptide sequence are found to have human NKT cell stimulating activity, as determined by T cell biology techniques, mutation or deletion of hydrophobic aminoacid residues may be carried out for residues belonging to one or to both of the sequences.

The peptides or polypeptides of the invention can be produced by recombinant expression in, e.g., bacterial cells (e.g. *Escherichia coli*), yeast cells (e.g., *Pichia* species, *Hansenula* species, *Saccharomyces* or *Schizosaccharomyces* species), insect cells (e.g. from *Spodoptera frugiperda* or *Trichoplusia ni*), plant cells or mammalian cells (e.g., CHO, COS cells). The construction of the therefore required suitable expression vectors (including further information such as promoter and termination sequences) involves meanwhile standard recombinant DNA techniques. Recombinantly produced peptides or polypeptides of the invention can be derived from a larger precursor protein, e.g., via enzymatic cleavage of enzyme cleavage sites inserted adjacent to the N- and/or C-terminus of the peptide or polypeptide, followed by suitable purification.

In view of the limited length of some of the peptides of the invention, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine. Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry which is amply known to the skilled person. In addition, peptides can be linked to each other to form longer peptides using a ligation strategy (chemoselective coupling of two unprotected peptide fragments) as originally described by Kent (Schnolzer & Kent (1992) *Int. J. Pept. Protein Res.* 40, 180-193) and reviewed for example in Tam et al. (2001) *Biopolymers* 60, 194-205. This provides the potential to achieve protein synthesis which is beyond the scope of SPPS. Many proteins with the size of 100-300 residues have been synthesized successfully by this method.

The physical and chemical properties of a peptide or polypeptide of the invention (e.g. solubility, stability) is examined to determine whether the peptide is/would be suitable for use in therapeutic compositions. Typically this is optimized by adjusting the sequence of the peptide. Optionally, the peptide can be modified after synthesis (chemical modifications e.g. adding/deleting functional groups) using techniques known in the art.

The production of genetically-modified organisms relies on methods well known for those skilled in the art, including cloning, site-directed mutagenesis and growth.

The present invention also relates to nucleic acid sequences encoding the peptides or polypeptides of the present invention and methods for their use, e.g., for recombinant expression or in gene therapy. In particular, said nucleic acid sequences are capable of expressing peptides of the invention.

In gene therapy, recombinant nucleic acid molecules encoding the peptides or polypeptides of the present invention can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognized by the cell normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilizing endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding a peptide according to the invention is provided. In particular embodiments, the vector is generated such that the nucleic acid molecule sequence is expressed only in a specific tissue. Methods of achieving tissue-specific gene expression are well known in the art, e.g., by placing the sequence encoding an immunogenic peptide of the invention under control of a promoter, which directs expression of the peptide specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for a peptide or polypeptide according to the invention may be used in gene therapy.

The medicament of the invention is usually, but not necessarily (for instance proteins produced by genetically-modified organisms which are used for food, feed, or to which said subject is exposed to systemic or inhalation route), a (pharmaceutical) formulation comprising as active ingredient at least one of the peptides or polypeptides of the invention, a gene therapeutic vector capable of expressing said peptide or polypeptide. Apart from the active ingredient(s), such formulation will comprise at least one of a (pharmaceutically acceptable) diluent. Typically, pharmaceutically acceptable compounds can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated.

The medicament or pharmaceutical composition of the invention may need to be administered to a subject in need as part of a prophylactic or therapeutic regimen comprising multiple administrations of said medicament or composition. Said multiple administrations usual occur sequentially and the time-interval between two administrations can vary and will be adjusted to the nature of the active ingredient and the nature of the condition to be prevented or treated. The amount of active ingredient given to a subject in need of a single administration can also vary and will depend on factors such as the physical status of the subject (as for instance weight and age), the status of the condition to be prevented or treated, and the experience of the treating doctor, physician or nurse.

The term "diluents" refers for instance to physiological saline solutions. The term "pharmaceutically acceptable carrier" means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the active ingredients.

Peptides or polypeptides, homologues or derivatives thereof according to the invention (and their physiologically acceptable salts or pharmaceutical compositions all included in the term "active ingredients") may be administered by any route appropriate to the condition to be prevented or treated and appropriate for the compounds, here the peptide or polypeptide to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the condition to be prevented or treated.

The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Viral vectors for the purpose of gene therapy or gene vaccination are highly amenable to modifications by means of recombinant nucleic acid technology. In view of the above, a skilled person will further easily envisage that the elimination of the viral vector NKT-cell epitope as applied in the peptides or polypeptides and their uses according to the invention can be introduced immediately in the viral vector itself. Hence, the invention further encompasses modified viral vectors defined as isolated viral vectors characterized in that CD1d binding motifs have been eliminated by aminoacid substitution or deletion.

The present invention will now be illustrated by means of the following examples, which are provided without any limiting intention. Furthermore, all references described herein are explicitly included herein by reference.

EXAMPLES

Example 1: Coagulation Factor VIII

Patients suffering from hemophilia A lack sufficient amounts of factor VIII (FVIII), which is the reason for uncontrolled bleeding tendency. Such patients are treated by infusions of FVIII purified from plasma source or produced by recombinant technology. Administration of FVIII results in the formation of specific antibodies, which in more or less 30% of the cases inhibit the function of FVIII as a coagulation cofactor.

Using an algorithm, we identified within the sequence of the FVIII molecule 3 sequences bearing a CD1d binding sequence, which matched the [FWTHY]-$X_2X_3$-[ILMV]-$X_5X_6$-[FWTHY] sequence motif. These motifs are located in the A1 and A3 domains, respectively:

FCHISSH in A1 domain (aminoacids 309-315, SEQ ID1)
FWKVQHH in A3 domain (aminoacids 1816-1822, SEQ ID2)
FHAINGY in A3 domain (aminoacids 1918-1924, SEQ ID3)

These sequences have in common (underlined) an aromatic residue (phenylalanine, F) in position 1, an aliphatic residue (isoleucine, I, or valine, V) in position 4, and an aromatic residue (histidine, H, or tyrosine, Y) in position 7.

To determine whether these sequences could activate NKT cells in vivo, FVIII (2 IU) was injected intravenously to hemophilia A mice on 4 occasions separated by a 1-week interval. Hemophilia A mice produce no FVIII due to a stop codon introduced in the FVIII gene in exon 16.

Mice were sacrificed 10 days after the last injection, the spleen was removed and CD4+ T cells were prepared by magnetic bead sorting. NKT cells are characterized by expression of CD4 and recognition of antigen presented by CD1d molecule. A tetramer of CD1d was obtained from a commercial supplier and loaded with 15 aminoacid long FVIII peptides, which included peptides containing SEQ ID1, SEQ ID2 and SEQ ID3. Significant binding of CD1d tetramers loaded with these peptides was observed, indicating that these 3 peptides were able to bind to CD1d and that injection of FVIII elicited activation of NKT cells. Representative results are given in FIG. 1.

Further, direct immunization with peptides containing a CD1d motif (peptides of SEQ ID1, SEQ ID2 or SEQ ID3) was sufficient as to elicit the activation of NKT cells and production of antibodies to FVIII. Prominent activation was observed with peptide of SEQ ID1. Representative results are given in FIG. 2.

Bone marrow chimeras were constructed in which hemophilia A mice were first irradiated and reconstituted with the bone marrow of mice lacking NKT cells, namely CD1d knocked-out mice. In the absence of NKT cells, mice were unable to produce significant amounts of antibodies to FVIII, and virtually no antibodies inhibiting the function of FVIII (FIG. 3).

The A1 domain of FVIII was produced by recombinant technology in its natural sequence or with a substitution of F309 and H315 by serine (polypeptide of SEQ ID4). FVIII A1 domains in natural sequence or SEQ ID4 were used to immunize separate groups of mice. The results showed that substitution of F309 and H315 by S (SEQ ID4) was sufficient to prevent activation of NKT cells as assessed from spleen CD4+ T cells as described above.

The A3 domain of FVIII was produced by recombinant technology in its natural sequence or with a substitution of F1816 and H1822 by serine (polypeptide of SEQ ID 5). FVIII A3 domains in natural sequence or SEQ ID5 were used to immunize separate groups of mice. The results showed that substitution of F1816 and H1822 by S (SEQ ID5) was sufficient to prevent activation of NKT cells as assessed from spleen CD4+ T cells as described above.

A B domain-deleted FVIII molecule in its natural sequence elicited activation of NKT cells (see above). A FVIII molecule with 4 aminoacid substitutions was prepared containing F309S, H315S, F1816S and F1918S (SEQ ID6). Intravenous injections of such mutated FVIII in hemophilia A mice did not result in the formation of antibodies to FVIII and, consequently, no antibodies inhibiting the function of FVIII.

It was therefore concluded that:

(1) FVIII naturally contains several CD1d binding motifs;

(2) these CD1d motifs are functional and elicit activation of NKT cells;

(3) activation of NKT cells is a requisite for the production of antibodies to FVIII;

(4) elimination of the CD1d motifs by aminoacid substitution is sufficient to eliminate the production of anti-F VIII antibodies It should be clear for those skilled in the art that the invention also applies to animals made transgenic for the production of coagulation factors such as factor IX.

DETAILED DESCRIPTION OF THE DRAWINGS

FIG. 1

NKT cells recognize factor VIII epitopes presented by CD1d

Hemophilia A mice were immunized with 2 IU Factor VIII on 4 occasions separated by one week. The spleen was then removed and CD4+ T cells were prepared by magnetic bead sorting. A fluorochrome-labeled tetramer of CD1d was obtained from a commercial supplier and loaded with 15 aminoacid long FVIII peptides, which included peptides containing SEQ ID1, ID2 and ID3. Loading was carried out at room temperature overnight in the dark.

Tetramers were then incubated for 30 minutes at 4° C. with the CD4+ T cell population and the cell suspension was analyzed by Facs.

The figure shows that CD1d tetramers loaded with peptide of SEQ ID1 (44pept in the figure) are recognized by NKT cells. CD1d ctl(−) shows the % of NKT cells recognizing unloaded tetramers. CD1d ctl (+) shows the % of NKT cells recognizing tetramers loaded with alpha-gal ceramide, which recruits all NKT cells. Up to 45% of NKT cells recognize 44pept, which is compatible with the absence of polymorphism at CD1d level and very limited polymorphism at the level of the NKT T cell receptor.

FIG. 2

Immunization of hemophilia A mice with a CD1d-restricted peptides elicits anti-factor VIII antibodies Hemophilia A mice were immunized 3 times subcutaneously with 50 μg of an equimolar mixture of peptides of SEQ ID1 (44pept) and peptide of SEQ ID2 (256pept) adsorbed on aluminum hydroxyde. A control group received physiological serum instead of peptides. Plasma was taken 10 days after the last immunization and assessed for the presence of anti-Factor VIII antibodies, using a direct binding assay. Briefly, Factor VIII (10 IU/ml) was insolubilized on polystyrene plates, which were washed and incubated with a 1/10 dilution of plasma. After a further washing, a HRP-labeled goat anti-mouse antiserum was added, followed by an enzyme substrate. Colour development was read as OD.

The figure shows that hemophilia A mice immunized with peptides of SEQ ID1 and of SEQ ID2 develop antibodies to Factor VIII.

FIG. 3

Hemophilia A mice reconstituted with bone marrow from CD1d KO mice do not produce antibodies to Factor VIII Hemophilia A mice were lethally irradiated and reconstituted with the bone marrow of CD1d KO mice ($5\times10^6$/mouse), which lack NKT cells. Six weeks after bone marrow reconstitution the mice received 4 IV injections of 2 IU/ml separated by one week. Mice were bled 10 days after the last immunization and the plasma was assayed for the presence of anti-Factor VIII antibodies using a direct binding assay as described in the legend of FIG. 2. A control group of irradiated hemophilia A mice was reconstituted with a normal bone marrow.

The figure indicates that, although control mice produce high concentrations of anti-FVIII antibodies after the fourth injection of Factor VIII (left panel), mice reconstituted with the bone marrow of NKT cell deficient mice did not (right panel).

Example 2: Adenovirus 5 Viral Vectors

Viral vectors are commonly used for gene therapy and gene vaccination. One of the most common of these viral vectors is derived from adenovirus, serotype 5. Adenoviruses (Ad) are non-enveloped viruses possessing a linear, double-stranded DNA genome of about 35 kb. Human Ad5 has a capsid consisting of 3 major structural proteins: hexon, penton, and fiber. Neutralizing antibodies are raised towards hexon proteins. Such antibodies are very common in humans as a consequence of viral infection. The presence of such antibodies blocks the entry of the viral vector and, consequently, prevents expression of the transgene protein carried by the vector. Anti-Ad5 antibodies are generated in the course of an adaptive response, which depends on activation of CD4+ T cells specific for epitopes presented in the context of MHC class II molecules.

It is known that Ad5 activates the innate immune system, though the precise mechanism by which it occurs and the location where it takes place remain unclear. Yet, activation of the innate immune system could be a required step for neutralizing antibodies to be formed.

Using algorithms, we identified 7 aminoacid sequences matching with the general motif [FWTHY]-X$_2$X$_3$-[ILMV]-X$_5$X$_6$-[FWTHY] of a CD1d binding sequence (SEQ ID7, with motifs underlined) in hexon 6.

Mice were injected intravenously with 10$^9$ PFU Ad5 vector on 3 occasions at 10-day intervals. CD4+ T cells were then prepared from the spleen by magnetic bead sorting. CD4+ T cells were incubated with CD1d tetramers loaded with peptides corresponding to each of the 7 sequences identified. It showed that a significant proportion (±10%) of CD4+ NKT cells were labeled by tetramers, indicating that Ad5 vector injections activated NKT cells specific for the peptide of SEQ ID7. In addition, such mice produced specific antibodies of the IgG2a isotype, characteristic of neutralizing antibodies in the mouse.

A viral vector was prepared which contained a substitution of [FW] by serine S for each of the 7 aminoacid sequences identified. This mutated viral vector (SEQ ID8, with underlined motifs) was used to immunize animals according to the same protocol as described above for the natural sequence. The proportion of NKT cells as assessed using tetramers loaded with the peptide in natural sequence (SEQ ID7) was <1% and the concentration of Ad5 virus specific antibodies was significantly reduced (up to 10-fold).

It was therefore concluded that substitution of F to S in each P1 location of CD1d binding motifs was sufficient as to reduce NKT cell activation and thereby reduce the production of anti-Ad5 antibodies.

Example 3: Genetically-Modified Proteins

Proteins to which subjects are exposed by way of inhalation or ingestion are frequently eliciting unwanted reactions in predisposed subjects. Allergic asthma affects millions of people across the world. Food allergy on the other hand has an overall prevalence of ±2.5% in the general population. Allergens either airborne, ingested or penetrating the skin could share properties by which they activate NKT cells.

One of the most common food allergen is apple (*Malus domesticus*), and allergenicity is almost exclusively borne by the Mal d 1 protein, a 159 aminoacid long protein, which protects the plant against infectious agents. A sequence motif was identified using computer algorithms, which corresponds to the general motif [FWTHY]-X$_2$X$_3$-[ILMV]-X$_5$X$_6$-[FWTHY] of a CD1d binding sequence.

FKLIESY corresponding to aminoacids 144-150 of Mal d 1 (SEQ ID9)

A recombinant form of Mal d 1, in which F144 and Y150 were mutated in S was produced by genetic engineering. The recombinant form of Mal d 1 therefore encompasses peptide of sequence:

SKLIESS (SEQ ID10)

Synthetic peptides corresponding to SEQ ID9 and SEQ ID10 were produced. Their capacity to activate NKT cells was determined in vitro using human dendritic cells derived from peripheral blood monocytes of an individual sensitized to Mal d 1. Dendritic cells loaded with each one of the two peptides were incubated in the presence of NKT cells obtained from the same individual by sorting peripheral lymphocytes using specific markers such as CD4 and NKG2D. It was observed that NKT cells incubated with peptide of SEQ ID9 activated a significant proportion of NKT cells, while the mutated peptide of SEQ ID10 did not. Additionally, human CD1d tetramers loaded with peptides of SEQ ID9 were recognized by a significant proportion of NKT cells, but tetramers loaded with the mutated peptide of SEQ ID10 were recognized by less than 1% of NKT cells.

The two F144S and Y150S mutations are introduced directly in clonal cells by site-directed mutagenesis. The full organism is then produced by conventional growth strategies. Apples produced by this GMO do not elicit allergic reactions.

One specific application of the peptides or polypeptides of the present invention is celiac disease (gluten intolerance). This disease is among the most commons in human beings and is related to T cell activation to gliadin epitopes which are presented in the context of MHC class II determinants. A genetic susceptibility has been described, with human beings carrying the HLA-DQ2 or DQ8 class II determinant being predisposed to disease. These class II determinants present peptides which have been submitted to deamidation by transglutaminase. However, these events are the results of intestinal inflammatory reaction, likely related to the innate immune system.

Gliadins are monomers of 250-300 aminoacid residues. A search for the general motif [FW]-XX-[ILM]-XX-[FWTHY] of a CD1d binding sequence using computer algorithms identified such sequence (SEQ ID11, see listing of sequences) in alpha-gliadin. A mutated form of alpha-gliadin was then produced in which the F residue of the motif was substituted by a S residue (SEQ ID12, see addendum).

The same procedure as for Mal d 1 was followed to show that, although polypeptide of SEQ ID11 activated a significant proportion of NKT cells when presented by antigen-presenting dendritic cells, the mutated form of the polypeptide (SEQ ID12) failed to do so. As for Mal d 1, human CD1d tetramers loaded with a synthetic peptide representing the motif identified in the polypeptide of SEQ ID11 were recognized by NKT cells, while tetramers loaded with the mutated form of the motif as shown in SEQ ID12 were not.

The mutation was introduced directly in clonal cells by site-directed mutagenesis. The full organism was then produced by conventional growth strategies. Cereals containing the mutated form of gliadin do not elicit reactions of intolerance.

It should be obvious for those skilled in the art that the present invention can also be applied to proteins which are added to, for instance, genetically-modified organisms to increase their resistance to insecticides, pesticides or any other modifications judged to be beneficial. Such modifications carry the risk of creating new CD1d binding motifs.

Additional examples of genetically-modified proteins with reduced allergenicity/immunogenicity are:
- food allergens such as soybean, peanut and fruits of the Rosaceous family
- milk proteins
- airborne allergens such as latex (*Hevea brasiliensis*), pollens of grasses such as Rye grass (*Lolium perenne*), Timothy (*Phleum pratense*) or Kentucky blue grass (*Poa pratensis*)
- fish parvalbumin
- honey bee phospholipase A2

It should also be clear for the one skilled in the art that the invention extends to methods by which peptides or polypeptides of the invention are produced, including the production of transgenic plants and animals.

Example 4: Allergen Der p 1

Der p 1 is a cysteine protease which is the main allergen of the so-called house dust mite (HDM), *D. pteronyssinus*. Sensitization to HDM is by far the commonest trigger of allergic asthma and rhinitis worldwide. Der p 1 contains 3 motifs matching the general CD1d binding motif [FWTHY]-$X_2X_3$-[ILMV]-$X_5X_6$-[FWTHY], as identified using computer algorithms and which are:

SEQ ID13: FSGVAAT aminoacids 38-44 of Der p 1
SEQ ID14: HSAIAAVI aminoacids 135-141 of Der p 1
SEQ ID15: YPYVVIL aminoacids 216-222 of Der p 1

Peptides of SEQ ID13, SEQ ID14 and SEQ ID15 were synthesized and used to load CD1d tetramers.

BALB/c mice were submitted to intranasal administration of Der p 1, using 50 μl of saline containing 100 μg of Der p 1. This challenge procedure was repeated twice on three consecutive days at one-week interval. The mice were sacrificed 5 days after the last nasal instillation and the spleen was removed. CD4+ T cells were purified by magnetic bead sorting and incubated in the presence of the CD1d tetramers loaded with peptides of SEQ ID13, SEQ ID14 or SEQ ID15. By fluorescence-activated cell sorter (facs) determination, it was observed that a significant percentage of cells (±10%) were stained with the tetramers, identifying them as CD4+ NKT cells. It was therefore concluded that peptides of SEQ ID13, SEQ ID14 and SEQ ID15 were functional in binding to CD1d and in being recognized by NKT cells.

CD4+ T cells obtained from the above experiments were incubated in culture medium in the presence of an antigen-presenting cell which expresses the CD1d molecule. Such cells are commercially available, as for instance the JAWS2 cells, which do not express MHC class II determinants. JAWS2 cells were loaded with Der p 1 and presentation of Der p 1-derived epitopes by CD1d was evaluated by measuring the production of cytokines such as IFN-gamma and IL-4 as markers of NKT activation. It could be observed that a significant production of cytokines was present, confirming that Der p 1 contained epitopes presented by CD1d molecules.

Next, a mutated form of Der p 1 was prepared by genetic engineering, in which the 3 aminoacid residues predicted to be in position P1 for CD binding of peptides of SEQ ID13, SEQ ID14 and SEQ ID15 were substituted by serine. The mutated Der p 1 (SEQ ID16) was used for nasal instillation as described above with Der p 1 in natural sequence (SEQ ID17). In such a case, no significant binding of CD4+ T cell splenocytes was observed when incubated with the tetramers loaded with peptide of SEQ ID13, peptide of SEQ ID14 or peptide of SEQ ID15, indicating that the mutated Der p 1 had lost its capacity to activate NKT cells specific for these peptides.

Further, mutated Der p 1 (SEQ ID16) was used to load JAWS2 cells and tested for its capacity to activate NKT cells. For this experiment, NKT cells were used as obtained from mice immunized with Der p 1 in either natural or mutated configuration. The production of IFN-gamma and IL-4 was taken as an indication of NKT activation. It was observed that NKT cells obtained from mice immunized with natural sequence Der p 1 failed to be activated when incubated in the presence of JAWS2 cells loaded with mutated Der p 1.

It was therefore concluded that Der p 1 in natural sequence contained functional CD1d restricted T cell epitopes activating NKT cells. Further, elimination of such functional CD1d-restricted epitopes by mutation was sufficient to eliminate NKT cell activation.

Example 5: Antibodies

Antibodies are used as therapeutic agents in a large number of indications, from chronic inflammatory diseases such as rheumatoid arthritis (e.g., anti-TNF-alpha antibodies) or allergic asthma (e.g. anti-IgE antibodies), to tumors (e.g., anti-CD20 antibodies). More than 120 therapeutic antibodies are presently used for clinical applications at various stages from preclinical to phase III trials and accepted for routine clinical practice.

Therapeutic antibodies are either chimeric or fully humanized, which contains sequence of foreign origin only in the complementarity determining regions of the variable parts. A minority of such antibodies are derived from the human repertoire and, as such, considered as poorly immunogenic. However, antibodies towards the therapeutic antibody, even when directly derived from the human repertoire, are produced by a majority of the patients under treatment, with, in a significant proportion of the cases, the production of antibodies neutralizing the activity of the therapeutic agent.

A search for epitopes matching the CD1d binding motif in human IgG antibody sequence was carried out using computer algorithms. One of such motif was identified in the CH2 region (second domain of the heavy chain constant part) of each of the 4 IgG subclass (IgG1, IgG2, IgG3 and IgG4) and a second motif was identified in the CH3 loop of IgG1, IgG2 and IgG4:

```
SEQ ID 18:
YRVVSVL (CH2 of IgG1 and IgG4)

SEQ ID 19:
FRVVSVL (CH2 of IgG2 and IgG3)

SEQ ID 20:
HEALHNH (CH3 loop of IgGL IgG2 and IgG4)
```

Synthetic peptides corresponding to SEQ ID18, SEQ ID19 and SEQ ID20 were produced and used to load human CD1d tetramers as for the examples above (see for instance example 4 for allergen Der p 1). Peripheral blood cells were obtained by venous puncture of patients who had received an injection of a therapeutic antibody during the previous 5 days. CD4+ T cells were purified by magnetic bead sorting. The cells were then incubated with tetramers loaded with peptides of SEQ ID18, SEQ ID19 or SEQ ID20. Analysis by facs identifies a significant proportion of NKT cells (±10%) labeled by tetramers.

Monoclonal human antibodies of the IgG4 isotype were derived from the peripheral blood B lymphocytes by transformation with the Epstein-Barr virus. The genomic sequence of such antibodies was obtained from transformed B cells. A viral vector containing the corresponding cDNA sequence was constructed and used for transfection of CHO cells. All these methods are known in the art (see for instance, Jacquemin et al Blood 92: 496-506, 1998).

The hydrophobic aminoacid residues located in position 1 in the peptides of SEQ ID18 and SEQ ID20 were mutated to a serine and the mutated antibody produced by transfected CHO cells.

Peripheral blood CD4+ T cells obtained as above were exposed in culture medium to human dendritic cells (derived from human peripheral blood monocytes by methods known in the art) and loaded with either the antibody in natural configuration (SEQ ID21) or its mutated counterpart (SEQ ID22). After culturing the cells with CD4+ T cells for 5 to 7 days, the population of CD4+ T cells activated by either natural or mutated antibody was evaluated. CD4+ NKT cells were separated from CD4+ T cells using an antibody to NKG2D, a surface marker associated with NK or NKT cells only.

It was observed that CD4+ T cells and NKT cells were activated when the antibody in natural sequence was used (SEQ ID21), while the mutated form of the antibody (SEQ ID22) only activate class II restricted CD4+ T cells and not NKT cells.

It was concluded that human IgG antibodies contained epitopes corresponding to the [FWTHY]-$X_2X_3$-[ILMV]-$X_5X_6$-[FWTHY] motif, having the capacity to be recognized by and to activate NKT cells. Further, mutation of key hydrophobic aminoacid residues within such motif was sufficient to prevent activation of NKT cells.

It should be understood that the examples provided here are not exhaustive and that combinations of proteins or peptides containing various numbers of aminoacid substitutions or deletions can be envisioned. For instance, in example 1, various combinations of substitution of hydrophobic aminoacids can be delineated.

```
SEQ ID 1
Factor VIII aminoacids 309-315 (human)
FCHISSH

SEQ ID 2
Factor VIII aminoacids 1816-1822 (human)
FWKVQHH

SEQ ID 3
Factor VIII aminoacids 1918-1924 (human)
FHAINGY

SEQ ID 4
Factor A1 domain (mutations F309S and H315S underlined) (human)
    1       ATRRYY LGAVELSWDYMQSDLGELP VDAR FPP RV P K S FPF

41       NTS VVYKKT LFVE F T VHLFNI AKPR P PWMGLLGPTI QA EV

81       YDT VVITLKNMASHPVSLHAVGVS Y W K ASEGAEYDDQTSQ

121       REK EDDK VFPGGSHTYVWQVLKE N G P MASDPLCLTYSYLS

161       HVD LVK DLNSGLIG AL LVCRE GSLA K E KTQ TL HKFILLFA

201       VFD EGKSWHSE TKN SLMQDRDAASARAWPKWITVNGYVNR

241       SLP GLIGCH R KSV YWH VIG MGTT PEV HSIF LEG HTFL VRN

281       HRQ AS LEI SPIT FLT AQTLLM DL GQFL LSC HIS SS QH DGM

321       EAY VKV DS CPEEP QLRMKNNE EAED YDDDLTDSEMDVVRF

361       D DDN SPSFI Q IRS VA KK HPKTW VHYIA AEEEDW DYAP LVL

401       APDDR SYKS QYLN NGPQ RIGRK YKK VRF MAYT DETFKTRE

441       AIQ H ES G ILGPLLYGE VG D TLL II FK NQ AS RP YNI YP H GI

481       TD VR PLYSR R LPK GVKHLK DFP ILP GEIFK YK WTV TVEDG

521       PTK SDPRCLTRYYS SFVNMERDLASG

SEQ ID 5
Factor VIII A3 domain (mutations F1816S and Hi822S underlined) (human)
 1637       SQNPPVLKRHQREITRTTLQSDQEEIDYDDTISVEMKKED

1677       FDIYDEDENQSPRSFQKKTRHYFIAAVERLWDYGMSSSPH

1717       VLRNRAQSGSVPQFKKVVFQEFTDGSFTQPLYRGELNEHL

1757       GLLGPYIRAEVEDNIMVTFRNQASRPYSFYSSLISYEEDQR

1798       QGAEPRKNFVKPNETKTYSWKVQHSMAPTKDEFDCKAW

1836       AYFSDVDLEKDVHSGLIGPLLVCHTNTLNPAHGRQVTVQE
```

```
1876  FALFFTIFDETKSWYFTENMERNCRAPCNIQMEDPTFKEN

1916  YRFHAINGYIMDTLPGLVMAQDQRIRWYLLSMGSNENIFIS

1956  IHFSGHVFTVRKKEEYKMALYNLYPGVFETVEMLPSKAGI

1996  WRVECLIGEHLHAGMSTLFLVYSNKCQTPLGMASGEIMDF

2036  QITASGQYGQWAPKLARLHYSGSINAWSTKEPFSWIKVDL

2076  LAPMIIHGIKTQGARQKFSSLYISQFIIMYSLDGKKWQTY

2116  RGNSTGTLMVFFGNVDSSGIKHNIFNPPIIARYIRLIIPTH

2156  YSIRSTLRMELMGCDLNSCSMPLGMESKAISDAQITASSY

2196  FTNMFATWSPSKARLHLQGRSNAWRPQVNNPKEWLQVDFQ

2236  KTMKVTGVTTQGVKSLLTSMYVKEFLISSSQDGHQWTLFF

2276  QNGKVKVFQGNQDSFTPVVNSLDPPLLTRYLRIHPQSWVH

2316  QIALRMEVLGCEAQDLY*

SEQ ID 6
Factor VIII (mutations F309S, H315S, F1816S and F1918S underlined) (human)
ATRRYYLGAVELSWDYMQSDLGELPVDARFPPRVPKSFPFNTSVVYKKTL
FVEFTVHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR
KSVYWHVIGMGTTPEVHSIFLEGHTFLVRNHRQASLEISPITFLTAQTLL
MDLGQFLLSCHISSSQHDGMEAYVKVDSCPEEPQLRMKNNEEAEDYDDDL
TDSEMDVVRFDDDNSPSFIQIRSVAKKHPKTWVHYIAAEEEDWDYAPLVL
APDDRSYKSQYLNNGPQRIGRKYKKVRFMAYTDETFKTREAIQUESGILG
PLLYGEVGDTLLIIFKNQASRPYNIYPHGITDVRPLYSRRLPKGVKHLKD
FPILPGEIFKYKWTVTVEDGPTKSDPRCLTRYYSSFVNMERDLASGLIGP
LLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNR
GMTALLKVSSCDKNTGDYYEDSYEDISAYLLSKNNAIEPRSFSQNSRHPS
TRQKQFNATTIPENDIEKTDPWFAHRTPMPKIQNVSSSDLLMLLRQSPTP
HGLSLSDLQEAKYETFSDDPSPGAIDSNNSLSEMTHFRPQLHHSGDMVFT
PESGLQLRLNEKLGTTAATELKKLDFKVSSTSNNLISTIPSDNLAAGTDN
TSSLGPPSMPVHYDSQLDTTLFGKKSSPLTESGGPLSLSEENNDSKLLES
GLMNSQESSWGKNVSSTESGRLFKGKRAHGPALLTKDNALFKVSISLLKT
NKTSNNSATNRKTHIDGPSLLIENSPSVWQNILESDTEFKKVTPLIHDRM
LMDKNATALRLNHMSNKTTSSKNMEMVQQKKEGPIPPDAQNPDMSFFKML
FLPESARWIQRTHGKNSLNSGQGPSPKQLVSLGPEKSVEGQNFLSEKNKV
VVGKGEFTKDVGLKEMVFPSSRNLFLTNLDNLHENNTHNQEKKIQEEIEK
KETLIQENVVLPQIHTVTGTKNFMKNLFLLSTRQNVEGSYEGAYAPVLQD
FRSLNDSTNRTKKHTAHFSKKGEEENLEGLGNQTKQIVEKYACTTRISPN
TSQQNFVTQRSKRALKQFRLPLEETELEKRIIVDDTSTQWSKNMKHLTPS
TLTQIDYNEKEKGAITQSPLSDCLTRSHSIPQANRSPLPIAKVSSFPSIR
PIYLTRVLFQDNSSHLPAASYRKKDSGVQESSHFLQGAKKNNLSLAILTL
EMTGDQREVGSLGTSATNSVTYKKVENTVLPKPDLPKTSGKVELLPKVHI
YQKDLFPTETSNGSPGHLDLVEGSLLQGTEGAIKWNEANRPGKVPFLRVA
TESSAKTPSKLLDPLAWDNHYGTQIPKEEWKSQEKSPEKTAFKKKDTILS
LNACESNHAIAAINEGQNKPEIEVTWAKQGRTERLCSQNPPVLKRHQREI
TRTTLQSDQEEIDYDDTISVEMKKEDFDIYDEDENQSPRSFQKKTRHYFI
AAVERLWDYGMSSSPHVLRNRAQSGSVPQFKKVVFQEFTDGSFTQPLYRG
ELNEHLGLLGPYIRAEVEDNIMVTFRNQASRPYSFYSSLISYEEDQRQGA
EPRKNFVKPNETKTYSWKVQHHMAPTKDEFDCKAWAYFSDVDLEKDVHSG
LIGPLLVCHTNTLNPAHGRQVTVQEFALFFTIFDETKSWYFTENMERNCR
APCNIQMEDPTFKENYRSHAINGYIMDTLPGLVMAQDQRIRWYLLSMGSN
ENIHSIHFSGHVFTVRKKEEYKMALYNLYPGVFETVEMLPSKAGIWRVEC
LIGEHLHAGMSTLFLVYSNKCQTPLGMASGHIRDFQITASGQYGQWAPKL
ARLHYSGSINAWSTKEPFSWIKVDLLAPMIIHGIKTQGARQKFSSLYISQ
FIIMYSLDGKKWQTYRGNSTGTLMVFFGNVDSSGIKHNIFNPPIIARYIR
LHPTHYSIRSTLRMELMGCDLNSCSMPLGMESKAISDAQITASSYFTNMF
ATWSPSKARLHLQGRSNAWRPQVNNPKEWLQVDFQKTMKVTGVTTQGVKS
LLTSMYVKEFLISSSQDGHQWTLFFQNGKVKVFQGNQDSFTPVVNSLDPP
LLTRYLRIHPQSWVHQIALRMEVLGCEAQDLY*GWPQHLPLPSPLPPQL
QGSVPPWLAFYLCAKS*QTLP*SLL
```

SEQ ID 7
Hexon, Human adenovirus 5, (CD1d binding motifs underlined): (virus)
MATPSMMPQWSYMHISGQDASEYLSPGLVQFARATETYFSLNNKFRNPTVAPTEEDV
TTDRSQRLTLRFIPVDREDTA
YSYKARFTLAVGDNRVLDMASTSFDIRGVLDRGPTFKPYSGTAYNALAPKGAPNPCE
WDEAATALEINLEEEDDDNE
DEVDEQAEQQKTHVFGQAPYSGINITKEGIQIGVEGQTPKYADKTFQPEPQIGESQWY
ETEINHAAGRVLKKTTPMK
PCYGSYAKPTNENGGQGILVKQQNGKLESQVEMQFFSTTEAAAGNGDNLTPKVVLY
SEDVDIETPDTHISYMPTIKE
GNSRELMGQQSMPNRPNYIAFRDNFIGLMYYNSTGNMGVLAGQASQLNAVVDLQD
RNTELSYQLLLDSIGDRTRYFS
MWKQAVDSYDPDVRIIENHGTEDELPNYCFPLGGVINTETLTKVKPKTGQENGWEK
DATEFSDKNEIRVGNNFAMEI
NLNANLWRNFLYSNIALYLPDKLKYSPSNVKISDNPNTYDYMNKRVVAPGLVDCYI
NLGARWSLDYMDNVNPFNEEHR
NAGLRYRSMLLGNGRYVPFHIQVPQKFFAIKNLLLLPGSYTYEWNFRKDVNMVLQSS
LGNDLRVDGASIKFDSICLY
ATFFPMAHNTASTLEAMLRNDTNDQSFNDYLSAANMLYPIPANATNVPISIPSRNWA
AFRGWAFTRLKTKETPSLGS
GYDPYYTYSGSIPYLDGTFYLNHTFKKVAITFDSSVSWPGNDRLLTPNEFEIKRSVDG
EGYNVAQCNNITKDWFLVQM
LANYNIGYQGFYIPESYKDRMYSFFRNFQPMSRQVVDDTKYKDYQQVGILHQHNNS
GFVGYLAPTMREGQAYPANFP
YPLIGKTAVDSITQKKFLCDRTLWRIPFSSNFMSMGALTDLGQNLLYANSAHALDMT
FEVDPMDEPTLLYVLFEVFD
VVRVHRPHRGVIETVYLRTPFSAGNATT SEQ ID 8
Hexon, Human *adenovirus* 5 (mutations of P1 anchoring residue underlined). (virus)
MATPSMMPQWSYMHISGQDASEYLSPGLVQFARATETSFSLNNKFRNPTVAPTHDV
TTDRSQRLTLRFIPVDREDTA
YSYKARFTLAVGDNRVLDMASTSFDIRGVLDRGPTFKPYSGTASNALAPKGAPNPCE
WDEAATALEINLEEEDDDNE
DEVDEQAEQQKTHVFGQAPSSGINITKEGIQIGVEGQTPKYADKTFQPEPQIGESQWY
ETEINHAAGRVLKKTTPMK
PCYGSYAKPTNENGGQGILVKQQNGKLESQVEMQFFSTTEAAAGNGDNLTPKVVLY
SEDVDIETPDTHISYMPTIKE
GNSRELMGQQSMPNRPNYIAFRDNSIGLMYYNSTGNMGVLAGQASQLNAVVDLQD
RNTELSYQLLLDSIGDRTRYFS
MWKQAVDSYDPDVRIIENHGTEDELPNYCFPLGGVINTETLTKVKPKTGQENGWEK
DATEFSDKNEIRVGNNFAMEI
NLNANLWRNFLSSNIALYLPDKLKYSPSNVKISDNPNTYDYNINKRVVAPGLVDCYIN
LGARWSLDYMDNVNPFNHHR
NAGLRSRSMLLGNGRYVPFSIQVPQKSFAIKNLLLLPGSYTYEWNFRKDVNMVLQSS
LGNDLRVDGASIKSDSICLY
ATFFPMAHNTASTLEANILRNDTNDQSFNDYLSAANNILYPIPANATNVPISIPSRNWA
AFRGWASTRLKTKETPSLGS
GYDPYYTYSGSIPYLDGTFYLNHTSKKVAITFDSSVSWPGNDRLLTPNEFEIKRSVDG
EGYNVAQCNNITKDSFLVQM
LANYNIGYQGFYIPESYKDRMYSFFRNFQPMSRQVVDDTKYKDSQQVGILHQHNNS
GFVGYLAPTMREGQAYPANFP
SPLIGKTAVDSITQKKFLCDRTLWRIPFSSNSMSMGALTDLGQNLLYANSAHALDMT
FEVDPMDEPTLLYVLFEVSD
VVRVHRPSRGVIETVYLRTPFSAGNATT SEQ ID 9
Mal d 1, *malus domesticus*, aminoacids 144-150
FKLIESY SEQ ID 10
Mal d 1, *malus domesticus*, F144S and Y150S mutations underlined (vegetal)
SKLIESS SEQ ID 11
Alpha-Gliadin (CD1d binding motif underlined)
MVRVPVPQLQPQNPSQQQPQEQVPLVQQQQFPGQQQPFPPQQPYPQQPFPSQQPYL
QLQPFPQPQLPYPQPQLPY
PQPQLPYPQPQPFRPQQPYPQSQPQYSQPQQPISQQQQQQQQQQQKQQQQQQQQIL
QQILQQQLIPCRDVVLQQH
SIAYGSSQVLQQSTYQLVQQLCCQQLWQIPEQSRCQAIIINVVHAIILHQQQQQQQQQ
QQQPLSQVSFQQPQQQYPS
GQGSFQPSQQNPQAGSVQPQQLPQFEEIRNLALETLPAMCNVYIPPYCTIAPVGIFGT
NYR SEQ ID 12
Alpha-Gliadin (mutation underlined)
MVRVPVPQLQPQNPSQQQPQEQVPLVQQQQFPGQQQPFPPQQPYPQQPFPSQQPSL
QLQPFPQPQLPYPQPQLPY
PQPQLPYPQPQPFRPQQPYPQSQPQYSQPQQPISQQQQQQQQQQQKQQQQQQQQIL

```
QQILQQQLIPCRDVVLQQH
SIAYGSSQVLQQSTSQLVQQLCCQQLWQIPEQSRCQAISNVVHAIILHQQQQQQQQQ
QQQPLSQVSFQQPQQQYPS
GQGSFQPSQQNPQAQGSVQPQQLPQSEEIRNLALETLPAMCNVYIPPSCTIAPVGIFGT
NYR

SEQ ID 13
D. pteronyssinus Der p 1, aminoacids 38-44 (pyroglyphidae, Dermatophagoides
pteronyssinus, European house dust mite)
FSGVAAT SEQ ID 14
D. pteronyssinus Der p 1, aminoacids 135-141 (pyroglyphidae, Dermatophagoides
pteronyssinus, European house dust mite)
HSAIAAVI SEQ ID 15
D. pteronyssinus Der p 1, aminoacids 216-222 (pyroglyphidae, Dermatophagoides
pteronyssinus, European house dust mite)
YPYVVIL SEQ ID 16
Mature Der p 1 (mutations of P1 anchoring residues F38S, H135S and Y216S underlined)
(pyroglyphidae, Dermatophagoides pteronyssinus, European house dust mite)
ETNACSINGNAPAEIDLRQMRTVTPIRMQGGCGSCWASSGVAATESAYLAYRNQSLD
LAEQELVDCASQHGCHGDTI
PRGIEYIQHNGVVQESYYRYVAREQSCRRPNAQRFGISNYCQTYPPNVNKIREALAQT
SSAIAVIIGIKDLDAFRHY
DGRTIIQRDNGYQPNYHAVNIVGYSNAQGVDYWIVRNSWDTNWGDNGYGYFAANI
DLMMIEESPYVVIL SEQ ID 17
Mature Der p 1 (CD1d epitopes underlined): (pyroglyphidae, Dermatophagoides
pteronyssinus, European house dust mite)
ETNACSINGNAPAEIDLRQMRTVTPIRMQGGCGSCWAFSGVAATESAYLAYRNQSLD
LAEQELVDCASQHGCHGDTI
PRGIEYIQHNGVVQESYYRYVAREQSCRRPNAQREGISNYCQTYPPNVNKIREALAQT
HSAIAVIIGIKDLDAFRHY
DGRTIIQRDNGYQPNYHAVNIVGYSNAQGVDYWIVRNSWDTNWGDNGYGYFAANI
DLMMIEEYPYVVIL SEQ ID 18
IgG antibody, CH2 domain of IgG1 and IgG4 (human)
YRVVSVL SEQ ID 19
IgG antibody, CH2 domain of IgG2 and IgG3 (human)
FRVVSVL SEQ ID 20
IgG antibody, CH3 domain of IgG1, IgG2 and IgG4 (human)
HEALHNH SEQ ID 21
Human IgG4 FC fragment (CD1d epitopes underlined) (human)
ASTKGPSVFPLAPCSRSTSESTAALGCLVKDYFPEPVTVSWNSGALTSGVHTFPAVLQ
SSGLYSLSSVVTVPSSSL
GTKTYTCNVDHKPSNTKVDKRVESKYGPPCPSCPAPEFLGGPSVFLFPPKPKDTLMIS
RTPEVTCVVVDVSQEDPE
VQFNANYVDGVEVHNAKTKPREEQFNSTYRVVSVLTVLHQDWLNGKEYKCKVSNK
GLPSSIEKTISKAKGQPREPQV
YTLPPSQEEMTKNQVSLTCLVKGFYPSDIAVEWESNGQPENNYKTTPPVLDSDGSFFL
YSRLTVDKSRWQEGNVFS
CSVNIFHALHNHYTQKSLSLSLGK SEQ ID 22
Human IgG4 FC fragment (mutated aminoacids underlined) (human)
ASTKGPSVFPLAPCSRSTSESTAALGCLVKDYFPEPVTVSWNSGALTSGVHTFPAVLQ
SSGLYSLSSVVTVPSSSL
GTKTYTCNVDHKPSNTKVDKRVESKYGPPCPSCPAPEFLGGPSVFLFPPKPKDTLMIS
RTPEVTCVVVDVSQEDPE
VQFNWYVDGVEVHNAKTKPREEQFNSTSRVVSVLTVLHQDWLNGKEYKCKVSNKG
LPSSIEKTISKAKGQPREPQV
YTLPPSQEEMTKNQVSLTCLVKGFYPSDIAVEWESNGQPENNYKTTPPVLDSDGSFFL
YSRLTVDKSRWQEGNVFS
CSVMSEALHNHYTQKSLSLSLGK
```

The invention claimed is:

1. An engineered peptide or polypeptide comprising SEQ ID NO:4 or SEQ ID NO:5.

2. A method for the production of an engineered peptide or polypeptide, comprising the steps of
providing a CD1d-binding peptide or polypeptide selected from the group consisting of an allofactor peptide or polypeptide, a viral vector peptide or polypeptide, a peptide or polypeptide of a genetically-modified organism, and a peptide or polypeptide vaccine for an allergen, which comprises one or more motifs consisting of [F/W/T/H/Y]-$X_2X_3$-[I/L/M/V]-$X_5X_6$-[F/W/T/H/Y] and binds to CD1d;
and substituting the [F/W/T/H/Y] amino acids at positions P1 and P7 of the motif by an amino acid different from [F/W/T/H/Y] to provide an engineered peptide or polypeptide,
wherein the binding to CD1d by the engineered peptide or polypeptide is reduced as compared with the CD1d-binding peptide,
and wherein the method further comprises the step of measuring if the engineered peptide or polypeptide has a reduced capacity to activate NKT cells as compared with the CD1d-binding peptide or polypeptide.

3. The method of claim 2, further comprising measuring the binding of the CD1d-binding peptide or polypeptide to CD1d, or the capacity of the CD1d-binding peptide or polypeptide to activate NKT cells.

4. The method of claim 3, further comprising the step of measuring if the engineered peptide or polypeptide has a reduced capacity to bind CD1d as compared with the CD1d-binding peptide or polypeptide.

* * * * *

SEQUENCE LISTING

<160> NUMBER OF SEQ ID NOS: 23

<210> SEQ ID NO 1
<211> LENGTH: 7
<212> TYPE: PRT
<213> ORGANISM: Homo sapiens

<400> SEQUENCE: 1

Phe Cys His Ile Ser Ser His
1               5

<210> SEQ ID NO 2
<211> LENGTH: 7
<212> TYPE: PRT
<213> ORGANISM: Homo sapiens

<400> SEQUENCE: 2

Phe Trp Lys Val Gln His His
1               5

<210> SEQ ID NO 3
<211> LENGTH: 7
<212> TYPE: PRT
<213> ORGANISM: Homo sapiens

<400> SEQUENCE: 3

Phe His Ala Ile Asn Gly Tyr
1               5

<210> SEQ ID NO 4
<211> LENGTH: 546
<212> TYPE: PRT
<213> ORGANISM: Homo sapiens

<400> SEQUENCE: 4

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Ser Cys His Ile Ser Ser Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly
545

<210> SEQ ID NO 5
<211> LENGTH: 696
<212> TYPE: PRT
<213> ORGANISM: Homo sapiens

<400> SEQUENCE: 5

Ser Gln Asn Pro Pro Val Leu Lys Arg His Gln Arg Glu Ile Thr Arg
1               5                   10                  15

```
Thr Thr Leu Gln Ser Asp Gln Glu Ile Asp Tyr Asp Thr Ile
            20                  25              30

Ser Val Glu Met Lys Lys Glu Asp Phe Asp Ile Tyr Asp Glu
        35                  40              45

Asn Gln Ser Pro Arg Ser Phe Gln Lys Lys Thr Arg His Tyr Phe Ile
50                  55                  60

Ala Ala Val Glu Arg Leu Trp Asp Tyr Gly Met Ser Ser Pro His
65                  70                  75                  80

Val Leu Arg Asn Arg Ala Gln Ser Gly Ser Val Pro Gln Phe Lys Lys
                85                  90                  95

Val Val Phe Gln Glu Phe Thr Asp Gly Ser Phe Thr Gln Pro Leu Tyr
            100                 105                 110

Arg Gly Glu Leu Asn Glu His Leu Gly Leu Leu Gly Pro Tyr Ile Arg
        115                 120                 125

Ala Glu Val Glu Asp Asn Ile Met Val Thr Phe Arg Asn Gln Ala Ser
    130                 135                 140

Arg Pro Tyr Ser Phe Tyr Ser Ser Leu Ile Ser Tyr Glu Glu Asp Gln
145                 150                 155                 160

Arg Gln Gly Ala Glu Pro Arg Lys Asn Phe Val Lys Pro Asn Glu Thr
                165                 170                 175

Lys Thr Tyr Ser Trp Lys Val Gln His Ser Met Ala Pro Thr Lys Asp
            180                 185                 190

Glu Phe Asp Cys Lys Ala Trp Ala Tyr Phe Ser Asp Val Asp Leu Glu
        195                 200                 205

Lys Asp Val His Ser Gly Leu Ile Gly Pro Leu Leu Val Cys His Thr
    210                 215                 220

Asn Thr Leu Asn Pro Ala His Gly Arg Gln Val Thr Val Gln Glu Phe
225                 230                 235                 240

Ala Leu Phe Phe Thr Ile Phe Asp Glu Thr Lys Ser Trp Tyr Phe Thr
                245                 250                 255

Glu Asn Met Glu Arg Asn Cys Arg Ala Pro Cys Asn Ile Gln Met Glu
            260                 265                 270

Asp Pro Thr Phe Lys Glu Asn Tyr Arg Phe His Ala Ile Asn Gly Tyr
        275                 280                 285

Ile Met Asp Thr Leu Pro Gly Leu Val Met Ala Gln Asp Gln Arg Ile
    290                 295                 300

Arg Trp Tyr Leu Leu Ser Met Gly Ser Asn Glu Asn Ile His Ser Ile
305                 310                 315                 320

His Phe Ser Gly His Val Phe Thr Val Arg Lys Lys Glu Glu Tyr Lys
                325                 330                 335

Met Ala Leu Tyr Asn Leu Tyr Pro Gly Val Phe Glu Thr Val Glu Met
            340                 345                 350

Leu Pro Ser Lys Ala Gly Ile Trp Arg Val Glu Cys Leu Ile Gly Glu
        355                 360                 365

His Leu His Ala Gly Met Ser Thr Leu Phe Leu Val Tyr Ser Asn Lys
    370                 375                 380

Cys Gln Thr Pro Leu Gly Met Ala Ser Gly His Ile Arg Asp Phe Gln
385                 390                 395                 400

Ile Thr Ala Ser Gly Gln Tyr Gly Gln Trp Ala Pro Lys Leu Ala Arg
                405                 410                 415

Leu His Tyr Ser Gly Ser Ile Asn Ala Trp Ser Thr Lys Glu Pro Phe
            420                 425                 430
```

```
Ser Trp Ile Lys Val Asp Leu Leu Ala Pro Met Ile His Gly Ile
            435                 440                 445

Lys Thr Gln Gly Ala Arg Gln Lys Phe Ser Ser Leu Tyr Ile Ser Gln
450                 455                 460

Phe Ile Ile Met Tyr Ser Leu Asp Gly Lys Lys Trp Gln Thr Tyr Arg
465                 470                 475                 480

Gly Asn Ser Thr Gly Thr Leu Met Val Phe Phe Gly Asn Val Asp Ser
                485                 490                 495

Ser Gly Ile Lys His Asn Ile Phe Asn Pro Pro Ile Ile Ala Arg Tyr
            500                 505                 510

Ile Arg Leu His Pro Thr His Tyr Ser Ile Arg Ser Thr Leu Arg Met
        515                 520                 525

Glu Leu Met Gly Cys Asp Leu Asn Ser Cys Ser Met Pro Leu Gly Met
530                 535                 540

Glu Ser Lys Ala Ile Ser Asp Ala Gln Ile Thr Ala Ser Ser Tyr Phe
545                 550                 555                 560

Thr Asn Met Phe Ala Thr Trp Ser Pro Ser Lys Ala Arg Leu His Leu
                565                 570                 575

Gln Gly Arg Ser Asn Ala Trp Arg Pro Gln Val Asn Asn Pro Lys Glu
            580                 585                 590

Trp Leu Gln Val Asp Phe Gln Lys Thr Met Lys Val Thr Gly Val Thr
        595                 600                 605

Thr Gln Gly Val Lys Ser Leu Leu Thr Ser Met Tyr Val Lys Glu Phe
    610                 615                 620

Leu Ile Ser Ser Ser Gln Asp Gly His Gln Trp Thr Leu Phe Phe Gln
625                 630                 635                 640

Asn Gly Lys Val Lys Val Phe Gln Gly Asn Gln Asp Ser Phe Thr Pro
                645                 650                 655

Val Val Asn Ser Leu Asp Pro Pro Leu Leu Thr Arg Tyr Leu Arg Ile
            660                 665                 670

His Pro Gln Ser Trp Val His Gln Ile Ala Leu Arg Met Glu Val Leu
        675                 680                 685

Gly Cys Glu Ala Gln Asp Leu Tyr
690                 695

<210> SEQ ID NO 6
<211> LENGTH: 2372
<212> TYPE: PRT
<213> ORGANISM: Homo sapiens

<400> SEQUENCE: 6

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110
```

Glu Tyr Asp Asp Gln Thr Ser Gln Arg Glu Lys Glu Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Ser Cys His Ile Ser Ser Ser Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

```
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                    565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                    645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
    690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                    725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
        755                 760                 765
Thr Asp Pro Trp Phe Ala His Arg Thr Pro Met Pro Lys Ile Gln Asn
    770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                    805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
        835                 840                 845
Phe Thr Pro Glu Ser Gly Leu Gln Leu Arg Leu Asn Glu Lys Leu Gly
    850                 855                 860
Thr Thr Ala Ala Thr Glu Leu Lys Lys Leu Asp Phe Lys Val Ser Ser
865                 870                 875                 880
Thr Ser Asn Asn Leu Ile Ser Thr Ile Pro Ser Asp Asn Leu Ala Ala
                    885                 890                 895
Gly Thr Asp Asn Thr Ser Ser Leu Gly Pro Pro Ser Met Pro Val His
            900                 905                 910
Tyr Asp Ser Gln Leu Asp Thr Thr Leu Phe Gly Lys Lys Ser Ser Pro
        915                 920                 925
Leu Thr Glu Ser Gly Gly Pro Leu Ser Leu Ser Glu Glu Asn Asn Asp
    930                 935                 940
Ser Lys Leu Leu Glu Ser Gly Leu Met Asn Ser Gln Glu Ser Ser Trp
```

-continued

```
                945                 950                 955                 960
            Gly Lys Asn Val Ser Ser Thr Glu Ser Gly Arg Leu Phe Lys Gly Lys
                            965                 970                 975
            Arg Ala His Gly Pro Ala Leu Leu Thr Lys Asp Asn Ala Leu Phe Lys
                        980                 985                 990
            Val Ser Ile Ser Leu Leu Lys Thr Asn Lys Thr Ser Asn Asn Ser Ala
                    995                 1000                1005
            Thr Asn Arg Lys Thr His Ile Asp Gly Pro Ser Leu Leu Ile Glu
                1010                1015                1020
            Asn Ser Pro Ser Val Trp Gln Asn Ile Leu Glu Ser Asp Thr Glu
                1025                1030                1035
            Phe Lys Lys Val Thr Pro Leu Ile His Asp Arg Met Leu Met Asp
                1040                1045                1050
            Lys Asn Ala Thr Ala Leu Arg Leu Asn His Met Ser Asn Lys Thr
                1055                1060                1065
            Thr Ser Ser Lys Asn Met Glu Met Val Gln Gln Lys Lys Glu Gly
                1070                1075                1080
            Pro Ile Pro Pro Asp Ala Gln Asn Pro Asp Met Ser Phe Phe Lys
                1085                1090                1095
            Met Leu Phe Leu Pro Glu Ser Ala Arg Trp Ile Gln Arg Thr His
                1100                1105                1110
            Gly Lys Asn Ser Leu Asn Ser Gly Gln Gly Pro Ser Pro Lys Gln
                1115                1120                1125
            Leu Val Ser Leu Gly Pro Glu Lys Ser Val Glu Gly Gln Asn Phe
                1130                1135                1140
            Leu Ser Glu Lys Asn Lys Val Val Val Gly Lys Gly Glu Phe Thr
                1145                1150                1155
            Lys Asp Val Gly Leu Lys Glu Met Val Phe Pro Ser Ser Arg Asn
                1160                1165                1170
            Leu Phe Leu Thr Asn Leu Asp Asn Leu His Glu Asn Asn Thr His
                1175                1180                1185
            Asn Gln Glu Lys Lys Ile Gln Glu Glu Ile Glu Lys Lys Glu Thr
                1190                1195                1200
            Leu Ile Gln Glu Asn Val Val Leu Pro Gln Ile His Thr Val Thr
                1205                1210                1215
            Gly Thr Lys Asn Phe Met Lys Asn Leu Phe Leu Leu Ser Thr Arg
                1220                1225                1230
            Gln Asn Val Glu Gly Ser Tyr Glu Gly Ala Tyr Ala Pro Val Leu
                1235                1240                1245
            Gln Asp Phe Arg Ser Leu Asn Asp Ser Thr Asn Arg Thr Lys Lys
                1250                1255                1260
            His Thr Ala His Phe Ser Lys Lys Gly Glu Glu Asn Leu Glu
                1265                1270                1275
            Gly Leu Gly Asn Gln Thr Lys Gln Ile Val Glu Lys Tyr Ala Cys
                1280                1285                1290
            Thr Thr Arg Ile Ser Pro Asn Thr Ser Gln Gln Asn Phe Val Thr
                1295                1300                1305
            Gln Arg Ser Lys Arg Ala Leu Lys Gln Phe Arg Leu Pro Leu Glu
                1310                1315                1320
            Glu Thr Glu Leu Glu Lys Arg Ile Ile Val Asp Asp Thr Ser Thr
                1325                1330                1335
            Gln Trp Ser Lys Asn Met Lys His Leu Thr Pro Ser Thr Leu Thr
                1340                1345                1350
```

```
Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740
```

```
Thr Gln Pro Leu Tyr Arg Gly Glu Leu Asn Glu His Leu Gly Leu
    1745             1750                 1755

Leu Gly Pro Tyr Ile Arg Ala Glu Val Glu Asp Asn Ile Met Val
    1760             1765                 1770

Thr Phe Arg Asn Gln Ala Ser Arg Pro Tyr Ser Phe Tyr Ser Ser
    1775             1780                 1785

Leu Ile Ser Tyr Glu Glu Asp Gln Arg Gln Gly Ala Glu Pro Arg
    1790             1795                 1800

Lys Asn Phe Val Lys Pro Asn Glu Thr Lys Thr Tyr Ser Trp Lys
    1805             1810                 1815

Val Gln His His Met Ala Pro Thr Lys Asp Glu Phe Asp Cys Lys
    1820             1825                 1830

Ala Trp Ala Tyr Phe Ser Asp Val Asp Leu Glu Lys Asp Val His
    1835             1840                 1845

Ser Gly Leu Ile Gly Pro Leu Leu Val Cys His Thr Asn Thr Leu
    1850             1855                 1860

Asn Pro Ala His Gly Arg Gln Val Thr Val Gln Glu Phe Ala Leu
    1865             1870                 1875

Phe Phe Thr Ile Phe Asp Glu Thr Lys Ser Trp Tyr Phe Thr Glu
    1880             1885                 1890

Asn Met Glu Arg Asn Cys Arg Ala Pro Cys Asn Ile Gln Met Glu
    1895             1900                 1905

Asp Pro Thr Phe Lys Glu Asn Tyr Arg Ser His Ala Ile Asn Gly
    1910             1915                 1920

Tyr Ile Met Asp Thr Leu Pro Gly Leu Val Met Ala Gln Asp Gln
    1925             1930                 1935

Arg Ile Arg Trp Tyr Leu Leu Ser Met Gly Ser Asn Glu Asn Ile
    1940             1945                 1950

His Ser Ile His Phe Ser Gly His Val Phe Thr Val Arg Lys Lys
    1955             1960                 1965

Glu Glu Tyr Lys Met Ala Leu Tyr Asn Leu Tyr Pro Gly Val Phe
    1970             1975                 1980

Glu Thr Val Glu Met Leu Pro Ser Lys Ala Gly Ile Trp Arg Val
    1985             1990                 1995

Glu Cys Leu Ile Gly Glu His Leu His Ala Gly Met Ser Thr Leu
    2000             2005                 2010

Phe Leu Val Tyr Ser Asn Lys Cys Gln Thr Pro Leu Gly Met Ala
    2015             2020                 2025

Ser Gly His Ile Arg Asp Phe Gln Ile Thr Ala Ser Gly Gln Tyr
    2030             2035                 2040

Gly Gln Trp Ala Pro Lys Leu Ala Arg Leu His Tyr Ser Gly Ser
    2045             2050                 2055

Ile Asn Ala Trp Ser Thr Lys Glu Pro Phe Ser Trp Ile Lys Val
    2060             2065                 2070

Asp Leu Leu Ala Pro Met Ile Ile His Gly Ile Lys Thr Gln Gly
    2075             2080                 2085

Ala Arg Gln Lys Phe Ser Ser Leu Tyr Ile Ser Gln Phe Ile Ile
    2090             2095                 2100

Met Tyr Ser Leu Asp Gly Lys Lys Trp Gln Thr Tyr Arg Gly Asn
    2105             2110                 2115

Ser Thr Gly Thr Leu Met Val Phe Phe Gly Asn Val Asp Ser Ser
    2120             2125                 2130

Gly Ile Lys His Asn Ile Phe Asn Pro Pro Ile Ile Ala Arg Tyr
```

2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr Gly Trp Pro Leu Gln His Leu Pro Leu Pro Ser
    2330                2335                2340

Pro Leu Pro Pro Gln Leu Gln Gly Ser Val Pro Pro Trp Leu Ala
    2345                2350                2355

Phe Tyr Leu Cys Ala Lys Ser Gln Thr Leu Pro Ser Leu Leu
    2360                2365                2370

<210> SEQ ID NO 7
<211> LENGTH: 952
<212> TYPE: PRT
<213> ORGANISM: Human adenovirus type 5

<400> SEQUENCE: 7

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Ser Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

-continued

```
Ala Pro Asn Pro Cys Glu Trp Asp Glu Ala Ala Thr Ala Leu Glu Ile
    130                 135                 140
Asn Leu Glu Glu Glu Asp Asp Asp Asn Glu Asp Glu Val Asp Glu Gln
145                 150                 155                 160
Ala Glu Gln Gln Lys Thr His Val Phe Gly Gln Ala Pro Tyr Ser Gly
                165                 170                 175
Ile Asn Ile Thr Lys Glu Gly Ile Gln Ile Gly Val Glu Gly Gln Thr
            180                 185                 190
Pro Lys Tyr Ala Asp Lys Thr Phe Gln Pro Glu Pro Gln Ile Gly Glu
        195                 200                 205
Ser Gln Trp Tyr Glu Thr Glu Ile Asn His Ala Ala Gly Arg Val Leu
    210                 215                 220
Lys Lys Thr Thr Pro Met Lys Pro Cys Tyr Gly Ser Tyr Ala Lys Pro
225                 230                 235                 240
Thr Asn Glu Asn Gly Gly Gln Gly Ile Leu Val Lys Gln Gln Asn Gly
                245                 250                 255
Lys Leu Glu Ser Gln Val Glu Met Gln Phe Phe Ser Thr Thr Glu Ala
            260                 265                 270
Ala Ala Gly Asn Gly Asp Asn Leu Thr Pro Lys Val Val Leu Tyr Ser
        275                 280                 285
Glu Asp Val Asp Ile Glu Thr Pro Asp Thr His Ile Ser Tyr Met Pro
    290                 295                 300
Thr Ile Lys Glu Gly Asn Ser Arg Glu Leu Met Gly Gln Gln Ser Met
305                 310                 315                 320
Pro Asn Arg Pro Asn Tyr Ile Ala Phe Arg Asp Asn Phe Ile Gly Leu
                325                 330                 335
Met Tyr Tyr Asn Ser Thr Gly Asn Met Gly Val Leu Ala Gly Gln Ala
            340                 345                 350
Ser Gln Leu Asn Ala Val Val Asp Leu Gln Asp Arg Asn Thr Glu Leu
        355                 360                 365
Ser Tyr Gln Leu Leu Asp Ser Ile Gly Asp Arg Thr Arg Tyr Phe
    370                 375                 380
Ser Met Trp Lys Gln Ala Val Asp Ser Tyr Asp Pro Asp Val Arg Ile
385                 390                 395                 400
Ile Glu Asn His Gly Thr Glu Asp Glu Leu Pro Asn Tyr Cys Phe Pro
                405                 410                 415
Leu Gly Gly Val Ile Asn Thr Glu Thr Leu Thr Lys Val Lys Pro Lys
            420                 425                 430
Thr Gly Gln Glu Asn Gly Trp Glu Lys Asp Ala Thr Glu Phe Ser Asp
        435                 440                 445
Lys Asn Glu Ile Arg Val Gly Asn Asn Phe Ala Met Glu Ile Asn Leu
    450                 455                 460
Asn Ala Asn Leu Trp Arg Asn Phe Leu Tyr Ser Asn Ile Ala Leu Tyr
465                 470                 475                 480
Leu Pro Asp Lys Leu Lys Tyr Ser Pro Ser Asn Val Lys Ile Ser Asp
                485                 490                 495
Asn Pro Asn Thr Tyr Asp Tyr Met Asn Lys Arg Val Val Ala Pro Gly
            500                 505                 510
Leu Val Asp Cys Tyr Ile Asn Leu Gly Ala Arg Trp Ser Leu Asp Tyr
        515                 520                 525
Met Asp Asn Val Asn Pro Phe Asn His His Arg Asn Ala Gly Leu Arg
530                 535                 540
Tyr Arg Ser Met Leu Leu Gly Asn Gly Arg Tyr Val Pro Phe His Ile
```

```
545                 550                 555                 560
    Gln Val Pro Gln Lys Phe Phe Ala Ile Lys Asn Leu Leu Leu Pro
                    565                 570                 575
    Gly Ser Tyr Thr Tyr Glu Trp Asn Phe Arg Lys Asp Val Asn Met Val
                    580                 585                 590
    Leu Gln Ser Ser Leu Gly Asn Asp Leu Arg Val Asp Gly Ala Ser Ile
                    595                 600                 605
    Lys Phe Asp Ser Ile Cys Leu Tyr Ala Thr Phe Pro Met Ala His
                610                 615                 620
    Asn Thr Ala Ser Thr Leu Glu Ala Met Leu Arg Asn Asp Thr Asn Asp
    625                 630                 635                 640
    Gln Ser Phe Asn Asp Tyr Leu Ser Ala Asn Met Leu Tyr Pro Ile
                    645                 650                 655
    Pro Ala Asn Ala Thr Asn Val Pro Ile Ser Ile Pro Ser Arg Asn Trp
                    660                 665                 670
    Ala Ala Phe Arg Gly Trp Ala Phe Thr Arg Leu Lys Thr Lys Glu Thr
                    675                 680                 685
    Pro Ser Leu Gly Ser Gly Tyr Asp Pro Tyr Tyr Thr Tyr Ser Gly Ser
                690                 695                 700
    Ile Pro Tyr Leu Asp Gly Thr Phe Tyr Leu Asn His Thr Phe Lys Lys
    705                 710                 715                 720
    Val Ala Ile Thr Phe Asp Ser Ser Val Ser Trp Pro Gly Asn Asp Arg
                    725                 730                 735
    Leu Leu Thr Pro Asn Glu Phe Glu Ile Lys Arg Ser Val Asp Gly Glu
                    740                 745                 750
    Gly Tyr Asn Val Ala Gln Cys Asn Met Thr Lys Asp Trp Phe Leu Val
                    755                 760                 765
    Gln Met Leu Ala Asn Tyr Asn Ile Gly Tyr Gln Gly Phe Tyr Ile Pro
                770                 775                 780
    Glu Ser Tyr Lys Asp Arg Met Tyr Ser Phe Phe Arg Asn Phe Gln Pro
    785                 790                 795                 800
    Met Ser Arg Gln Val Val Asp Asp Thr Lys Tyr Lys Asp Tyr Gln Gln
                    805                 810                 815
    Val Gly Ile Leu His Gln His Asn Asn Ser Gly Phe Val Gly Tyr Leu
                    820                 825                 830
    Ala Pro Thr Met Arg Glu Gly Gln Ala Tyr Pro Ala Asn Phe Pro Tyr
                    835                 840                 845
    Pro Leu Ile Gly Lys Thr Ala Val Asp Ser Ile Thr Gln Lys Lys Phe
                    850                 855                 860
    Leu Cys Asp Arg Thr Leu Trp Arg Ile Pro Phe Ser Ser Asn Phe Met
    865                 870                 875                 880
    Ser Met Gly Ala Leu Thr Asp Leu Gly Gln Asn Leu Leu Tyr Ala Asn
                    885                 890                 895
    Ser Ala His Ala Leu Asp Met Thr Phe Glu Val Asp Pro Met Asp Glu
                900                 905                 910
    Pro Thr Leu Leu Tyr Val Leu Phe Glu Val Phe Asp Val Val Arg Val
                    915                 920                 925
    His Arg Pro His Arg Gly Val Ile Glu Thr Val Tyr Leu Arg Thr Pro
                    930                 935                 940
    Phe Ser Ala Gly Asn Ala Thr Thr
    945                 950

<210> SEQ ID NO 8
```

<211> LENGTH: 952
<212> TYPE: PRT
<213> ORGANISM: Human adenovirus type 5

<400> SEQUENCE: 8

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Ser Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Ser Phe Asp Ile Arg Gly Val Leu Asp Arg Gly Pro Thr
            100                 105                 110

Phe Lys Pro Tyr Ser Gly Thr Ala Ser Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Ser Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Ala Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Ser Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Leu Asp Ser Ile Gly Asp Arg Thr Arg Tyr Phe
    370                 375                 380

Ser Met Trp Lys Gln Ala Val Asp Ser Tyr Asp Pro Asp Val Arg Ile

```
            385                 390                 395                 400
        Ile Glu Asn His Gly Thr Glu Asp Leu Pro Asn Tyr Cys Phe Pro
                        405                 410                 415

Leu Gly Gly Val Ile Asn Thr Glu Thr Leu Thr Lys Val Lys Pro Lys
                        420                 425                 430

Thr Gly Gln Glu Asn Gly Trp Glu Lys Asp Ala Thr Glu Phe Ser Asp
                        435                 440                 445

Lys Asn Glu Ile Arg Val Gly Asn Asn Phe Ala Met Glu Ile Asn Leu
        450                 455                 460

Asn Ala Asn Leu Trp Arg Asn Phe Leu Ser Ser Asn Ile Ala Leu Tyr
        465                 470                 475                 480

Leu Pro Asp Lys Leu Lys Tyr Ser Pro Ser Asn Val Lys Ile Ser Asp
                        485                 490                 495

Asn Pro Asn Thr Tyr Asp Tyr Met Asn Lys Arg Val Val Ala Pro Gly
                        500                 505                 510

Leu Val Asp Cys Tyr Ile Asn Leu Gly Ala Arg Trp Ser Leu Asp Tyr
                        515                 520                 525

Met Asp Asn Val Asn Pro Phe Asn His His Arg Asn Ala Gly Leu Arg
        530                 535                 540

Ser Arg Ser Met Leu Leu Gly Asn Gly Arg Tyr Val Pro Phe Ser Ile
        545                 550                 555                 560

Gln Val Pro Gln Lys Ser Phe Ala Ile Lys Asn Leu Leu Leu Leu Pro
                        565                 570                 575

Gly Ser Tyr Thr Tyr Glu Trp Asn Phe Arg Lys Asp Val Asn Met Val
                        580                 585                 590

Leu Gln Ser Ser Leu Gly Asn Asp Leu Arg Val Asp Gly Ala Ser Ile
                        595                 600                 605

Lys Ser Asp Ser Ile Cys Leu Tyr Ala Thr Phe Phe Pro Met Ala His
        610                 615                 620

Asn Thr Ala Ser Thr Leu Glu Ala Met Leu Arg Asn Asp Thr Asn Asp
        625                 630                 635                 640

Gln Ser Phe Asn Asp Tyr Leu Ser Ala Ala Asn Met Leu Tyr Pro Ile
                        645                 650                 655

Pro Ala Asn Ala Thr Asn Val Pro Ile Ser Ile Pro Ser Arg Asn Trp
                        660                 665                 670

Ala Ala Phe Arg Gly Trp Ala Ser Thr Arg Leu Lys Thr Lys Glu Thr
                        675                 680                 685

Pro Ser Leu Gly Ser Gly Tyr Asp Pro Tyr Tyr Thr Tyr Ser Gly Ser
                        690                 695                 700

Ile Pro Tyr Leu Asp Gly Thr Phe Tyr Leu Asn His Thr Ser Lys Lys
        705                 710                 715                 720

Val Ala Ile Thr Phe Asp Ser Ser Val Ser Trp Pro Gly Asn Asp Arg
                        725                 730                 735

Leu Leu Thr Pro Asn Glu Phe Glu Ile Lys Arg Ser Val Asp Gly Glu
                        740                 745                 750

Gly Tyr Asn Val Ala Gln Cys Asn Met Thr Lys Asp Ser Phe Leu Val
                        755                 760                 765

Gln Met Leu Ala Asn Tyr Asn Ile Gly Tyr Gln Gly Phe Tyr Ile Pro
                        770                 775                 780

Glu Ser Tyr Lys Asp Arg Met Tyr Ser Phe Phe Arg Asn Phe Gln Pro
        785                 790                 795                 800

Met Ser Arg Gln Val Val Asp Asp Thr Lys Tyr Lys Asp Ser Gln Gln
                        805                 810                 815
```

```
Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Ser
            835                 840                 845

Pro Leu Ile Gly Lys Thr Ala Val Asp Ser Ile Thr Gln Lys Lys Phe
            850                 855                 860

Leu Cys Asp Arg Thr Leu Trp Arg Ile Pro Phe Ser Ser Asn Ser Met
865                 870                 875                 880

Ser Met Gly Ala Leu Thr Asp Leu Gly Gln Asn Leu Leu Tyr Ala Asn
            885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Ser Asp Val Val Arg Val
            915                 920                 925

His Arg Pro Ser Arg Gly Val Ile Glu Thr Val Tyr Leu Arg Thr Pro
            930                 935                 940

Phe Ser Ala Gly Asn Ala Thr Thr
945                 950

<210> SEQ ID NO 9
<211> LENGTH: 7
<212> TYPE: PRT
<213> ORGANISM: Malus domestica

<400> SEQUENCE: 9

Phe Lys Leu Ile Glu Ser Tyr
1               5

<210> SEQ ID NO 10
<211> LENGTH: 7
<212> TYPE: PRT
<213> ORGANISM: Malus domestica

<400> SEQUENCE: 10

Ser Lys Leu Ile Glu Ser Ser
1               5

<210> SEQ ID NO 11
<211> LENGTH: 290
<212> TYPE: PRT
<213> ORGANISM: Homo sapiens

<400> SEQUENCE: 11

Met Val Arg Val Pro Val Pro Gln Leu Gln Pro Gln Asn Pro Ser Gln
1               5                   10                  15

Gln Gln Pro Gln Glu Gln Val Pro Leu Val Gln Gln Gln Gln Phe Pro
            20                  25                  30

Gly Gln Gln Gln Pro Phe Pro Pro Gln Gln Pro Tyr Pro Gln Pro Gln
            35                  40                  45

Pro Phe Pro Ser Gln Gln Pro Tyr Leu Gln Leu Gln Pro Phe Pro Gln
            50                  55                  60

Pro Gln Leu Pro Tyr Pro Gln Pro Gln Leu Pro Tyr Pro Gln Pro Gln
65                  70                  75                  80

Leu Pro Tyr Pro Gln Pro Gln Pro Phe Arg Pro Gln Gln Pro Tyr Pro
            85                  90                  95

Gln Ser Gln Pro Gln Tyr Ser Gln Pro Gln Gln Pro Ile Ser Gln Gln
            100                 105                 110
```

```
Gln Gln Gln Gln Gln Gln Gln Lys Gln Gln Gln Gln
    115                 120                 125

Gln Gln Gln Ile Leu Gln Ile Leu Gln Gln Leu Ile Pro Cys
    130                 135                 140

Arg Asp Val Val Leu Gln Gln His Ser Ile Ala Tyr Gly Ser Ser Gln
145                 150                 155                 160

Val Leu Gln Gln Ser Thr Tyr Gln Leu Val Gln Gln Leu Cys Cys
                    165                 170                 175

Gln Leu Trp Gln Ile Pro Glu Gln Ser Arg Cys Gln Ala Ile His Asn
                    180                 185                 190

Val Val His Ala Ile Ile Leu His Gln Gln Gln Gln Gln Gln Gln
                    195                 200                 205

Gln Gln Gln Gln Pro Leu Ser Gln Val Ser Phe Gln Gln Pro Gln Gln
    210                 215                 220

Gln Tyr Pro Ser Gly Gln Gly Ser Phe Gln Pro Ser Gln Asn Pro
225                 230                 235                 240

Gln Ala Gln Gly Ser Val Gln Pro Gln Gln Leu Pro Gln Phe Glu Glu
                    245                 250                 255

Ile Arg Asn Leu Ala Leu Glu Thr Leu Pro Ala Met Cys Asn Val Tyr
                    260                 265                 270

Ile Pro Pro Tyr Cys Thr Ile Ala Pro Val Gly Ile Phe Gly Thr Asn
                    275                 280                 285

Tyr Arg
    290

<210> SEQ ID NO 12
<211> LENGTH: 290
<212> TYPE: PRT
<213> ORGANISM: Homo sapiens

<400> SEQUENCE: 12

Met Val Arg Val Pro Val Pro Gln Leu Gln Pro Gln Asn Pro Ser Gln
1               5                   10                  15

Gln Gln Pro Gln Glu Gln Val Pro Leu Val Gln Gln Gln Gln Phe Pro
                20                  25                  30

Gly Gln Gln Gln Pro Phe Pro Pro Gln Gln Pro Tyr Pro Gln Pro Gln
            35                  40                  45

Pro Phe Pro Ser Gln Gln Pro Ser Leu Gln Leu Gln Pro Phe Pro Gln
        50                  55                  60

Pro Gln Leu Pro Tyr Pro Gln Pro Gln Leu Pro Tyr Pro Gln Pro Gln
65                  70                  75                  80

Leu Pro Tyr Pro Gln Pro Gln Pro Phe Arg Pro Gln Gln Pro Tyr Pro
                85                  90                  95

Gln Ser Gln Pro Gln Tyr Ser Gln Pro Gln Gln Pro Ile Ser Gln Gln
                100                 105                 110

Gln Gln Gln Gln Gln Gln Gln Gln Lys Gln Gln Gln Gln
    115                 120                 125

Gln Gln Gln Ile Leu Gln Gln Ile Leu Gln Gln Gln Leu Ile Pro Cys
    130                 135                 140

Arg Asp Val Val Leu Gln Gln His Ser Ile Ala Tyr Gly Ser Ser Gln
145                 150                 155                 160

Val Leu Gln Gln Ser Thr Ser Gln Leu Val Gln Gln Leu Cys Cys Gln
                    165                 170                 175

Gln Leu Trp Gln Ile Pro Glu Gln Ser Arg Cys Gln Ala Ile Ser Asn
                    180                 185                 190
```

```
Val Val His Ala Ile Ile Leu His Gln Gln Gln Gln Gln Gln Gln
        195                 200                 205

Gln Gln Gln Gln Pro Leu Ser Gln Val Ser Phe Gln Gln Pro Gln Gln
    210                 215                 220

Gln Tyr Pro Ser Gly Gln Gly Ser Phe Gln Pro Ser Gln Gln Asn Pro
225                 230                 235                 240

Gln Ala Gln Gly Ser Val Gln Pro Gln Gln Leu Pro Gln Ser Glu Glu
            245                 250                 255

Ile Arg Asn Leu Ala Leu Glu Thr Leu Pro Ala Met Cys Asn Val Tyr
            260                 265                 270

Ile Pro Pro Ser Cys Thr Ile Ala Pro Val Gly Ile Phe Gly Thr Asn
        275                 280                 285

Tyr Arg
    290

<210> SEQ ID NO 13
<211> LENGTH: 7
<212> TYPE: PRT
<213> ORGANISM: Dermatophagoides pteronyssinus

<400> SEQUENCE: 13

Phe Ser Gly Val Ala Ala Thr
1               5

<210> SEQ ID NO 14
<211> LENGTH: 8
<212> TYPE: PRT
<213> ORGANISM: Dermatophagoides pteronyssinus

<400> SEQUENCE: 14

His Ser Ala Ile Ala Ala Val Ile
1               5

<210> SEQ ID NO 15
<211> LENGTH: 7
<212> TYPE: PRT
<213> ORGANISM: Dermatophagoides pteronyssinus

<400> SEQUENCE: 15

Tyr Pro Tyr Val Val Ile Leu
1               5

<210> SEQ ID NO 16
<211> LENGTH: 223
<212> TYPE: PRT
<213> ORGANISM: Dermatophagoides pteronyssinus

<400> SEQUENCE: 16

Glu Thr Asn Ala Cys Ser Ile Asn Gly Asn Ala Pro Ala Glu Ile Asp
1               5                   10                  15

Leu Arg Gln Met Arg Thr Val Thr Pro Ile Arg Met Gln Gly Gly Cys
            20                  25                  30

Gly Ser Cys Trp Ala Ser Ser Gly Val Ala Ala Thr Glu Ser Ala Tyr
        35                  40                  45

Leu Ala Tyr Arg Asn Gln Ser Leu Asp Leu Ala Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
```

```
                85                  90                  95
Tyr Val Ala Arg Glu Gln Ser Cys Arg Arg Pro Asn Ala Gln Arg Phe
            100                 105                 110

Gly Ile Ser Asn Tyr Cys Gln Ile Tyr Pro Pro Asn Val Asn Lys Ile
            115                 120                 125

Arg Glu Ala Leu Ala Gln Thr Ser Ser Ala Ile Ala Val Ile Ile Gly
            130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
                165                 170                 175

Gly Tyr Ser Asn Ala Gln Gly Val Asp Tyr Trp Ile Val Arg Asn Ser
                180                 185                 190

Trp Asp Thr Asn Trp Gly Asp Asn Gly Tyr Gly Tyr Phe Ala Ala Asn
                195                 200                 205

Ile Asp Leu Met Met Ile Glu Glu Ser Pro Tyr Val Val Ile Leu
                210                 215                 220

<210> SEQ ID NO 17
<211> LENGTH: 223
<212> TYPE: PRT
<213> ORGANISM: Dermatophagoides pteronyssinus

<400> SEQUENCE: 17

Glu Thr Asn Ala Cys Ser Ile Asn Gly Asn Ala Pro Ala Glu Ile Asp
1               5                   10                  15

Leu Arg Gln Met Arg Thr Val Thr Pro Ile Arg Met Gln Gly Gly Cys
                20                  25                  30

Gly Ser Cys Trp Ala Phe Ser Gly Val Ala Ala Thr Glu Ser Ala Tyr
            35                  40                  45

Leu Ala Tyr Arg Asn Gln Ser Leu Asp Leu Ala Glu Gln Glu Leu Val
            50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
                85                  90                  95

Tyr Val Ala Arg Glu Gln Ser Cys Arg Arg Pro Asn Ala Gln Arg Phe
            100                 105                 110

Gly Ile Ser Asn Tyr Cys Gln Ile Tyr Pro Pro Asn Val Asn Lys Ile
            115                 120                 125

Arg Glu Ala Leu Ala Gln Thr His Ser Ala Ile Ala Val Ile Ile Gly
            130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
                165                 170                 175

Gly Tyr Ser Asn Ala Gln Gly Val Asp Tyr Trp Ile Val Arg Asn Ser
                180                 185                 190

Trp Asp Thr Asn Trp Gly Asp Asn Gly Tyr Gly Tyr Phe Ala Ala Asn
                195                 200                 205

Ile Asp Leu Met Met Ile Glu Glu Tyr Pro Tyr Val Val Ile Leu
                210                 215                 220

<210> SEQ ID NO 18
<211> LENGTH: 7
```

<212> TYPE: PRT
<213> ORGANISM: Homo sapiens

<400> SEQUENCE: 18

Tyr Arg Val Val Ser Val Leu
1               5

<210> SEQ ID NO 19
<211> LENGTH: 7
<212> TYPE: PRT
<213> ORGANISM: Homo sapiens

<400> SEQUENCE: 19

Phe Arg Val Val Ser Val Leu
1               5

<210> SEQ ID NO 20
<211> LENGTH: 7
<212> TYPE: PRT
<213> ORGANISM: Homo sapiens

<400> SEQUENCE: 20

His Glu Ala Leu His Asn His
1               5

<210> SEQ ID NO 21
<211> LENGTH: 327
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 22
<211> LENGTH: 327
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Ser Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
```

```
                    260                 265                 270
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met Ser Glu Ala Leu His Asn His Tyr Thr Gln Lys Ser
305                 310                 315                 320

Leu Ser Leu Ser Leu Gly Lys
                325

<210> SEQ ID NO 23
<211> LENGTH: 7
<212> TYPE: PRT
<213> ORGANISM: Artificial Sequence
<220> FEATURE:
<223> OTHER INFORMATION: CD1d Consensus
<220> FEATURE:
<221> NAME/KEY: MISC_FEATURE
<222> LOCATION: (1)..(1)
<223> OTHER INFORMATION: Xaa is Phe, Trp, Thr, His, or Tyr
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Xaa is Ile, Leu, Met, or Val
<220> FEATURE:
<221> NAME/KEY: MISC_FEATURE
<222> LOCATION: (5)..(5)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (7)..(7)
<223> OTHER INFORMATION: Xaa is Phe, Trp, Thr, His, or Tyr

<400> SEQUENCE: 23

Xaa Xaa Xaa Xaa Xaa Xaa Xaa
1               5
```